United States Patent

Ermann et al.

Patent Number: 5,266,593
Date of Patent: Nov. 30, 1993

[54] SUBSTITUTED PYRAN DERIVATIVES HAVING ANTIINFECTIVE ACTIVITY

[75] Inventors: Peter Ermann, Donaustauf; Henner Straub, Regensburg; Uwe D. Treuner, Etterzhausen; Jakob-Matthias Drossard, Tegernheim, all of Fed. Rep. of Germany

[73] Assignee: E. R. Squibb & Sons, Inc., Princeton, N.J.

[21] Appl. No.: 906,808

[22] Filed: Jun. 30, 1992

[51] Int. Cl.$^5$ ............... A61K 31/335; C07D 309/10
[52] U.S. Cl. ..................... 514/459; 549/419
[58] Field of Search .................. 549/419; 514/459

[56] References Cited

U.S. PATENT DOCUMENTS 4,952,604  8/1990  Hensens et al. ............... 514/459

FOREIGN PATENT DOCUMENTS 56-18592  2/1981  Japan .

OTHER PUBLICATIONS

Nakamura et al., C.A., 105:191,400z (1986)–Abstract of EP 188,384.
Miyazaki et al., C.A., 112:317,423f (1990)–Abstract of Chem. Pharm. Bull., 37(9), 2379-90 (1990).
J. P. Van Wauwe et al., "Is There a Case for P-450 Inhibitors in Cancer Treatment?", Journal of Medicinal Chemistry, vol. 32, No. 10 (Oct. 1989), pp. 2231-2239.
R. E. Schwartz et al., "Restricticin, A Novel Glycine-Containing Antifungal Agent", Journal of Antibiotics, vol. 44, No. 5, (May 1991), pp. 463-471.

Primary Examiner—Nicky Chan
Attorney, Agent, or Firm—Ellen K. Park

[57] ABSTRACT

Novel antibiotic substances, having the general formula

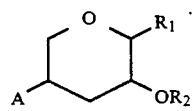

wherein A, $R_1$ and $R_2$ are as defined herein.

23 Claims, No Drawings

SUBSTITUTED PYRAN DERIVATIVES HAVING ANTIINFECTIVE ACTIVITY

SUMMARY OF THE INVENTION

In accordance with the present invention, novel compounds having antibiotic and cytochrome P450 inhibition activity are disclosed. These compounds have the general formula

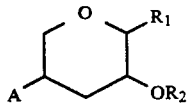

and pharmaceutically acceptable salts thereof.

As used in formula I, and throughout the specification, the symbols have the following meanings:

A is hydrogen or methyl;

$R_1$ is alkyl, alkenyl, arylalkyl, arylalkenyl, carboxy,

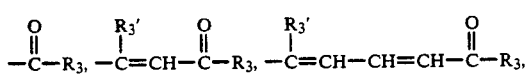

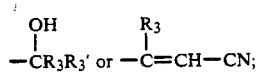

$R_2$ is hydrogen;

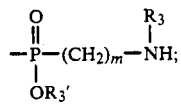

$R_3$ and $R_3'$ are independently hydrogen or alkyl; and m is an integer of 1 to 4.

DETAILED DESCRIPTION OF THE INVENTION

The present invention relates to the compounds of formula I and to pharmaceutical compositions employing such compounds. Listed below are definitions of various terms used to describe the compounds of the instant invention. These definitions apply to the terms as they are used throughout the specification (unless they are otherwise limited in specific instances) either individually or as part of a larger group.

The term "alkyl" refers to both straight and branched chain hydrocarbons, containing 1 to 12 carbon atoms in the normal chain, preferably 1 to 5 carbon atoms as well as such groups optionally substituted with one or more substituents selected from halogen, alkyl, alkylthio, hydroxy, amino, alkylamino, dialkylamino, alkoxy, trifluoromethyl and carboxy. The term "lower alkyl" as employed herein includes such alkyl groups as described above containing 1 to 4 carbon atoms in the normal chain.

The term "alkenyl" refers such groups as described above for alkyl, further containing at least one carbon to carbon double bond. Alkenyl groups having 5 to 10 carbon atoms in the normal chain are preferred.

The term "alkoxy" refers to such alkyl groups as described above, linked to an oxygen atom.

The term "aryl" refers to phenyl or phenyl substituted with halogen, alkyl, alkoxy, alkylthio, hydroxy, alkanoyl, nitro, amino, alkylamino, dialkylamino, cyano or trifluoromethyl groups. Phenyl and monosubstituted phenyl are preferred and phenyl is the most preferred.

The term "alkanoyl" refers to an alkyl group as described above, linked to a carbonyl group.

Compounds of formula I where $R_1$ is alkyl or arylalkyl are prepared by hydrogenating compounds of formula I where $R_1$ is alkenyl or arylalkenyl. Compounds of formula I where $R_1$ is alkenyl or arylalkenyl are prepared from the alcohols of formula

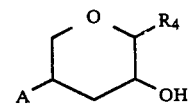

where $R_4$ is alkenyl or arylalkenyl.

An exemplary process for preparing the compounds of formula I where $R_1$ is alkenyl or arylakenyl and $R_2$ is

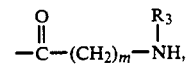

includes reacting an alcohol of formula I a compound of formula

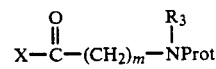

where X is a halogen or hydroxy in the presence of a coupling reagent such as dicyclohexyl carbodiimide or ethyl-3-(3-dimethylamino) propyl carbodiimide and Prot is a protecting group such as $-COOC_4H_9$ or $-COOC_2H_4-Si(CH_3)_3$ to provide the products of the formula

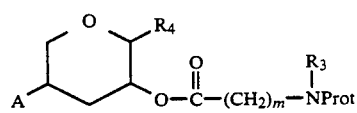

which form compounds of formula I after deprotection.

Alternatively, compounds of formula I where $R_1$ is alkenyl or arylalkenyl and $R_2$ is

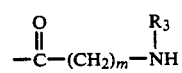

where $R_3$ is hydrogen), may be prepared by reacting an alcohol of formula II with compounds of the formula

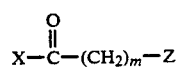

where Z is $-N_3$, halogen or O—L and L is hydrogen or a leaving group such as $-SO_2-CH_3$ or $-SO_2-C_6H_9-CH_3$ to form compounds of the formula

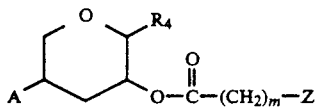

Those compounds of the formula VI where Z is halogen or O—L may then be converted by conventional methods to compounds of formula VI where Z is —N₃. Compounds of formula VI where Z is —N₃ may then be reduced by known methods to provide compounds of formula I.

To prepare compounds of formula I where R₁ is alkenyl or arylalkenyl and R₂ is

an alcohol of the formula II is reacted with phosgene or an equivalent thereof such as "diphosgene" (trichloromethyl chloroformate) or "triphosgene" (bistrichloromethyl carbonate) or with 4-nitrophenyl chloroformate to provide compounds of the formula

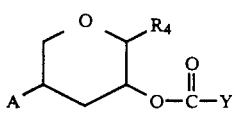

where Y is chlorine or —O—C₆H₄—p—NO₂. Compounds of formula VII may then be reacted with a hydrazine derivative such as

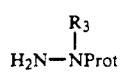

to provide compounds of the formula

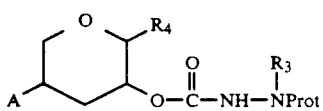

which form the compounds of formula I after deprotection.

To prepare compounds of formula I where R₁ is alkenyl or arylalkenyl and R₂ is

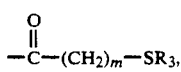

a compound of the formula

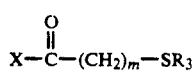

(or an S-protected form thereof when R₃ is hydrogen) is reacted with an alcohol of formula II to provide compounds of the formula

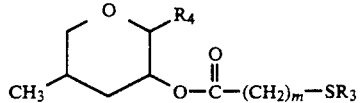

To prepare compounds of formula I where R₁ is alkenyl or arylalkenyl and R₂ is

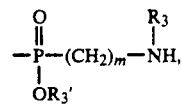

a compound of the formula

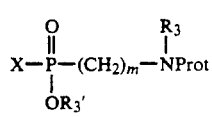

is reacted with an alcohol of formula II to provide compounds of the formula

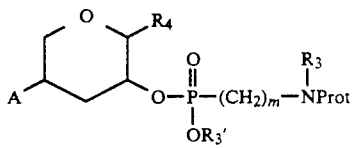

form the compounds of formula I after deprotection.

Alternatively, compounds of formula I where R₁ is alkenyl or arylalkenyl and R₂ is

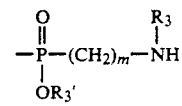

(R₃ is hydrogen), may be prepared by reacting an alcohol of formula II with compounds of the formula

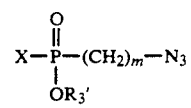

to form compounds of the formula

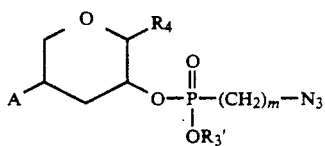

Compounds of formula XIV may then be reduced by known methods to provide compounds of formula I. Further, protected forms of compounds of formulae XI, XII, XIII and XIV, where the group R₃' has been replaced by a suitable protecting group, R$_x$ such as —CH₂CH₂Si(CH₃)₃ or —CH₂CN may be employed in the above reactions to form protected compounds of formula I.

Alternatively, compounds of formula XIV may be prepared by reacting an alcohol of formula II with compounds of the formula $$X-\underset{\underset{X}{\overset{\overset{O}{\|}}{P}}}{}-(CH_2)_m-N_3 \quad \text{XV}$$

to form compounds of the formula

XVI which are then reacted with lower alkyl alcohols such as methanol or ethanol to form compounds of formula XIV, where $R_3'$ is a lower alkyl.

To prepare a compounds of formula II, compounds of formula

XVII where Prot is a suitable protecting group such as —Si(CH$_3$)$_2$—R$_3$ are subjected to Wittig- or Horner-Emmons- reactions or to Peterson-olefination reactions using standard methodologies to form compounds of formula

XVIII which are then deprotected using standard procedures.

Alternatively, compounds of formula XVIII may be prepared stepwise from compounds of formula XVII via intermediates of formulae

XIX

XX

XXI

XXII where $R_3$ in formulae XIX to XXII is hydrogen. Intermediates of formulae XIX to XXII where $R_3$ is alkyl, may be prepared stepwise from compounds of formula

XXIII which may be prepared by reacting compounds of formula XVII with Grignard reagents such as alkyl-Mg-halogen to form compounds of the formula

XXIV which are then oxidized by reagents such as pyridinium chlorochromate.

Compounds of formula XVII, where A is hydrogen, are known from the literature (e.g.: K. C. Nicolaou et. al., J. Am. Chem. Soc. 1990, 112, 3040–3054).

An exemplary process for preparing compounds of formula XVII, where A is methyl, includes reducing compounds of formula

XXV to give alcohols of the formula

XXVI

After protection of the alcohol of formula XXVI by a suitable protecting group, compounds of the formula

XXVII are formed.

Compounds of the formula XXVII are then cleaved by an oxidating agent such as ozone to give aldehydes of the formula

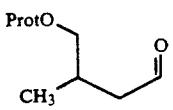
XXVIII which are then reacted in a Wittig-type reaction with compounds of the formula $(C_6H_5)_3P=CH-COO-R_5$ (where $R_5$ is alkyl) to give compounds of the formula

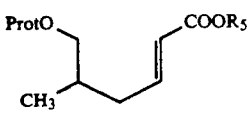
XXIX

Compounds of the formula XXIX are then reduced to give alcohols of the formula

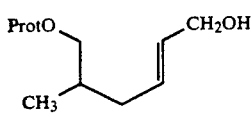
XXX which are then oxidized with alkylperoxides such as t-butyl peroxide in the presence of catalysts such as titanium isopropoxide and alkyl tartrates to give oxiranes of the formula

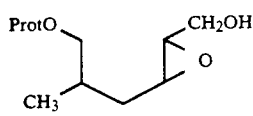
XXXI

Compounds of the formula XXXI are then oxidized to give aldehydes of the formula

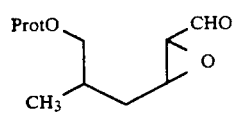
XXXII which are then reacted in a Wittig-type reaction with a compound of the formula $(C_6H_5)_3P=CH_2$ to give compounds of the formula

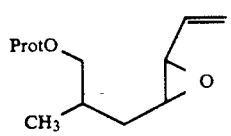
XXXIII

Compounds of the formula XXXIII can then be deprotected and then are treated with an acid such as camphorsulfonic acid or pyridinium toluene-4-sulfonate to give compounds of the formula

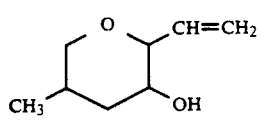
XXXIV

Protection of these compounds leads to compounds of the formula

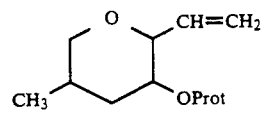
XXXV where Prot is a suitable protecting group. Finally, reaction with an oxidating agent such as ozone leads to compounds of formula XVII.

To form compounds of formula I where $R_1$ is other than alkyl, alkenyl, arylalkyl or arylalkenyl and $R_2$ is other than hydrogen, compounds of formula XVIII, where the $R_5$ side chain has been modified may be deprotected to form the corresponding alcohol and then used in reactions as the alcohol of formula II.

Compounds of formulas III, V and IX may be prepared by modifying (by standard methods) the corresponding acids of those compounds, which are commercially available. Compounds of formulas XI and XXV may be prepared by methods known to those skilled in the art or are commercially available.

Compounds of formula XIII may be prepared by conventional methods or are commercially available.

Compounds of formula XV where X is chlorine and m=1, may be prepared by standard procedures as described generally in Houben-Weyl "Methoden der organ.Chemie" Vol XII. One example of the preparation of a compound of formula XV where X is chlorine and m=1, is to react a compound of the formula

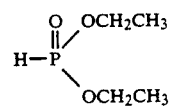
XXXVI with paraformaldehyde in the presence of a base such as triethylamine to form a compound having the formula

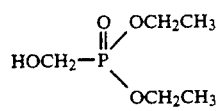
XXXVII which is then reacted with a leaving group forming reagent such as pTosCl and a base such as dimethylaminopyridine in an aprotic solvent such as dimethylformamide to form a compound of the formula

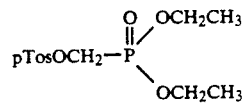
XXXVIII

A compound of formula XXXVIII is then reacted with an azide such as $NaN_3$ in an organic solvent such as dimethylformamide to form a compound of formula

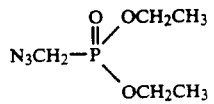
XXXIX which is then reacted with an alkylsilylhalide such as trimethylsilylbromide and then with a P—Cl bond forming reagent such as $(COCl)_2$ to form compounds of formula XV where m=1. Compounds of formula XV where X is other than chlorine and m is other than the integer 1 are prepared by known methods or are commercially available.

All diastereomers as well as geometrical isomers (E,Z-isomers) of compounds I resulting from substituents $R_1$ or $R_2$ carrying optical or geometrical isomery are within the scope of this invention.

Preferred compounds are those of the structures

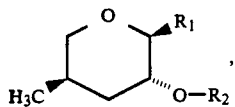

IA

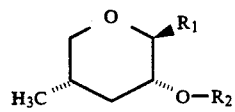

IB and

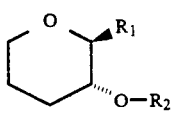

IC wherein $R_1$ is alkyl, alkenyl or arylalkenyl and $R_2$ is

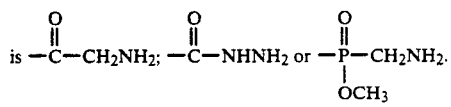

Most preferred are those compounds of formulae IA, IB or IC wherein $R_1$ is selected from

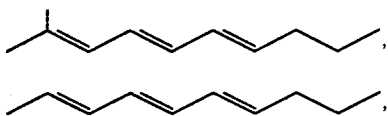

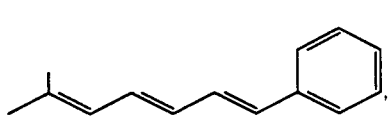

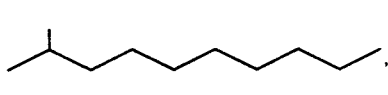

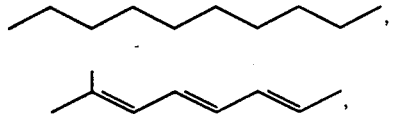

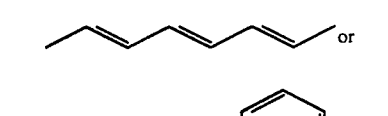

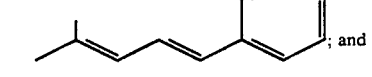

or

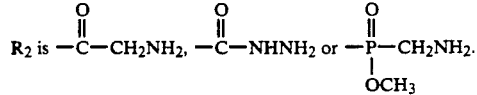
; and $R_2$ is
$-\overset{O}{\underset{\|}{C}}-CH_2NH_2$, $-\overset{O}{\underset{\|}{C}}-NHNH_2$ or $-\overset{O}{\underset{\underset{OCH_3}{|}}{\overset{\|}{P}}}-CH_2NH_2$.

The synthetic compounds of formula I and pharmaceutically acceptable salts thereof, can be used to combat fungal infections (particularly infections of Candida and other yeasts and filamentous fungi, such as Tricophyton, Microsporum, etc.) in domesticated animals and humans. In addition, these compounds have been found to inhibit cytochrome P450 enzymes, such as lanosterol demethylase. These compounds can therefore be used in a variety of ways including as an adrenal steroidogenesis inhibitor against infections caused by protozoa for the treatment of metastatic mammary carcinoma, in post-menopausal or ovariectomized women, in Cushing's syndrome, in breast, prostatic, endometrial, ovarian and pancreatic carcinomas, and as an inhibitor of aromatase or other cytochrome P450 enzymes. Based on this cytochrome P450 inhibition activity, the compounds of the present invention are also expected to be useful in the treatment of hypertension. These compounds can be administered topically, orally or parenterally. The dosage used of compounds of formula I or a pharmaceutically acceptable salt thereof will vary with the severity of the infection or disorder and the size of the host. For a human adult, daily doses of about 100 mg to 1 gm/day are exemplary.

Compounds of formula I, or salts thereof, may also be used in the treatment of fungal diseases of plants and may be used as plant growth regulators by inhibition of cytochrome P450 monooxygenases involved in the biosynthesis of gibberellin. Treatment with the compounds of formula I for these uses may be carried out by application to seed, foliage or to the soil.

The following examples and preparations describe the manner and process of making and using the invention and are illustrative rather than limiting. It should be understood that there may be other embodiments which fall within the spirit and scope of the invention as defined by the claims appended hereto.

EXAMPLE 1

Glycine, [2S-[2α(E,E,E)3β,5α]]Tetrahydro-5-methyl-2-(1-methyl-1,3,5-nonatrienyl)-2H-pyran-3-yl-ester A. (2R-trans)-3-[3-[[(1,1-Dimethylethyl)dimethylsilyl]oxy]-2-methylpropyl]oxirane-ethanol 1. 2-Methyl-4-penten-1-ol Under an argon atmosphere a 1M solution of lithium aluminium hydride in tetrahydrofuran (229.7 mL, 229.7 mmol) was added dropwise to a solution of 2-Methyl-4-pentenoic acid (31.8 g, 278.4 mmol) in 90 mL dry tetrahydrofuran. The solvent began to boil and after the addition, the mixture was stirred for an additional two hours. The mixture was then cooled with an ice bath and water (55 mL) and subsequently 1N sodium hydroxide solution (28 mL) were added with caution. After stirring for 30 minutes the resulting solids were filtered off with suction and the filtrate dried and evaporated to give the title compound as a colorless oil (24.7 g, 88.7%).

IR (film): 1640 (C=C), 3340 (OH) cm$^{-1}$ $^1$H-NMR (DMSO-d$_6$): δ=0.80 (d, 3H); 1.30–2.30 (m, 3H); 3.20 (td, 2H); 4.45 (t, 1H, OH); 4.85–5.10 (m, 2H); 5.55–6.0 (m, 1H); ppm.

2. 5-[[(1,1-Dimethylethyl)dimethylsilyl]oxy]-4-methyl-1-pentene

To a solution of the title 1 compound (61.3 g, 612.2 mmol) in dichloromethane (1.5 L) were added tert-butyldimethylsilyl chloride (184.5 g, 1.22 mol) and imidazole (83.3 g, 1.22 mol) and the mixture was stirred for three days at room temperature. Ater filtration, the filtrate was evaporated to yield the title compound as a colorless oil (123.0 g, 93.7%).

$^1$H-NMR (DMSO-d$_6$): δ=0.00 (s, 6H); 0.80 (d, 3H); 0.83 (s, 9H); 1.20-2.30 (m, 3H); 3.28 (m, 2H); 4.85-5.15 (m, 2H); 5.55-6.0 (m, 1H); ppm.

3. 4-[[(1,1-Dimethylethyl)dimethylsilyl]oxy]-3-methylbutanal

At −78° C., ozone was bubbled through a solution of the title 2 compound (61.5 g, 286.9 mmol) in dichloromethane (600 mL) until the solution turned violet. Excess ozone was expelled with nitrogen and then a solution of triphenylphosphine (75.1 g, 286.3 mmol) in dichloromethane (240 mL) was added dropwise at −78° C. The mixture was then allowed to warm to room temperature and the solvent was evaporated in vacuo. The residue was suspended in ether, cooled with an ice bath and the resulting solid (triphenylphosphine oxide) filtered off with suction. The filtrate was evaporated to give the crude title compound as an oil (73.8 g, quant.).

4. (E)-6-[[(1,1-Dimethylethyl)dimethylsilyl]oxy]-5-methyl-2-hexenoic acid, ethyl ester To a solution of the crude title 3 compound (73.8 g, max. 286.9 mmol) in tetrahydrofuran (800 mL) was added methoxycarbonylmethylene triphenylphosphorane (45.9 g, 286.9 mmol) and the mixture was heated to reflux for two hours and then stirred at room temperature for 16 hours. The solvent was evaporated and the residue suspended in ether and cooled. Triphenylphosphine oxide was filtered off and the filtrate concentrated in vacuo. The resulting crude compound (87.5 g) was chromatographed on silica gel with petroleum ether/ether (96:4) as eluent. The compound containing fractions were collected and evaporated to give the title compound (53.0 g, 67.7%) as a colorless oil and the (Z)-isomer of the title compound (6.9 g, 8.9%).

IR (film): 1655 (C=C), 1730 (CO) cm$^{-1}$ $^1$H-NMR (DMSO-d$_6$): δ=0.00 (s, 6H); 0.80 (d, 3H); 0.83 (s, 9H); 1.20-2.40 (m, 3H); 3.40 (d, 2H); 3.64 (s, 3H); 5.85 (dt, 1H); 6.89 (dt, 1H); ppm.

5. (E)-6-[[(1,1-Dimethylethyl)dimethylsilyl]oxy]-5-methyl-2-hexen-1-ol

At −78° C., a 1M solution of diisobutyl aluminium hydride in toluene (447.2 mL, 447.2 mmol) was added dropwise to a solution of the title 4 compound (53.0 g, 194.5 mmol) in dry tetrahydrofuran (230 mL). The mixture was allowed to warm to room temperature and was stirred an additional 30 minutes. Under cooling in an ice water bath (60 mL) and subsequently 1N sodium hydroxide solution (30 mL) were added dropwise. After stirring for 30 minutes the solids were filtered off and the filtrate dried and evaporated to give the title compound (45.2 g, 95.0%). This material was finally filtered over silica gel using ether/petroleum ether 1:4 (1.5 L) and then neat ether (1.5 L) as eluent. The title compound (41.8 g, 88.0%) was eluted with ether as a colorless oil. IR (film): 3340 (OH) cm$^{-1}$ $^1$H-NMR (CDCl$_3$): δ=0.00 (s, 6H); 0.85 (d, 3H); 0.87 (s, 9H); 1.20-2.30 (m, 3H); 3.40 (d, 2H); 4.09 (d, 2H); 5.75 (mc, 2H); ppm.

6. (2R-trans)-3-[3-[[(1,1-Dimethylethyl-dimethylsilyl]oxy]-2-methylpropyl]oxirane-ethanol To a solution of D-(−)-diethyl tartrate (1.23 g, 5.99 mmol) in dichloromethane (111 mL) was added at −20° C. and under an inert gas atmosphere, molsieve 4A (2.6 g, powder), titanium isopropoxide (1.46 g, 5.13 mmol) and dropwise a solution of the title 5 compound (20.9 g, 85.6 mmol) in dichloromethane (171 mL). After stirring for 30 minutes tert-butylhydroperoxide anhydrous (57.0 mL, 3M solution in toluene, 171.1 mmol) was added dropwise and the mixture was then stirred overnight at −20° C. and an additional three hours at −10° C. A precooled, freshly prepared solution of ferrous sulfate heptahydrate (28.2 g) and tartaric acid (8.6 g) in a total volume of 86 mL water was added to the mixture and the mixture was stirred for ten minutes. The phases were separated and the aqueous phase extracted once with dichloromethane. The combined organic phases were extracted with water and treated with precooled (0° C.) solution of 30% sodium hydroxide in saturated brine (9 mL). The two-phase mixture was stirred vigorously for one hour at 0° C. The phases were separated, the organic phase was dried and evaporated to give the title compound as a colorless oil (22.3 g, 100%).

IR (film): 3420 (OH) cm$^{-1}$

H-NMR (CDCl$_3$): δ=0.00 (s, 6H); 0.75 (s, 9H); 0.93, 0.95 (2d, 3H); 1.20-1.45 (m, 1H); 1.60-1.90 (m, 2H); 2.88 (mc, 1H, epoxide); 2.99 (mc, 1H, epoxide); 3.45 (mc, 2H, CH$_2$—Si); 3.60 (mc, 1H); 3.87 (mc, 1H); ppm.

B. (2R-trans)-2-[3-[[(1,1-Dimethylethyl)dimethylsilyl]oxy]-2-methylpropyl]-3-ethenyl-oxirane 1. (2S-trans)-3-[3-[[(1,1-Dimethylethyl)dimethylsilyl]oxy-2-methyl-propyl]oxiranecarboxaldehyde To a solution of the title A compound (28.1 g, 107.9 mmol) in dichloromethane (540 mL) was added dimethyl sulfoxide (99.7 g, 1.27 mol) and triethylamine (81.9 g, 0.81 mol). Sulfur trioxide pyridine complex (77.3 g, 485.5 mmol) was added at 0° C. in four portions within 30 minutes and the mixture was stirred for three hours at 0° C. Dichloromethane was distilled off in vacuo and the residue taken up in ether. The solution was washed with saturated ammonium chloride solution, dried and evaporated to give the crude title compound as a colorless oil (30.6 g, quant.).

IR (film): 1730 (CO) cm$^{-1}$ 2. (2R-trans)-2-[3-[[(1,1-Dimethylethyl)dimethylsilyl]oxy]-2-methylpropyl-3-ethenyl-oxirane At 0° C., under an inert gas atmosphere, a 1M solution of sodium bis(trimethyl-silyl)amide (161.8 mL, 161.8 mmol) in tetrahydrofuran was added dropwise to a solution of (methyl)triphenylphosphonium bromide (57.8 g, 161.85 mmol) in tetrahydrofuran (270 mL). After stirring for 30 minutes a solution of crude title 1 compound (30.6 g) in tetrahydrofuran (150 mL) was added dropwise and the mixture was stirred overnight at room temperature. The solvent was then removed in vacuo and the residue dissolved in ethyl acetate. The solution was washed four times with water, dried and evaporated. The residue was triturated with ether, stored in the refrigerator and the resulting solid (triphenylphosphine oxide) filtered off with suction. The filtrate was evaporated to give of the crude title compound (41.7 g) which was chromatographed on silica gel using petroleum ether/ether (98:2) as eluent. The compound containing fractions were collected and evaporated to give the title compound as a colorless oil (16.5 g, 59.5%).

$^1$H-NMR (CDCl$_3$): δ=0.00 (s, 6H); 0.85 (s, 9H); 0.92, 0.95 (2d, 3H); 1.15-1.40 (m, 1H); 1.60-1.90 (m, 2H); 2.82 (mc, 1H, epoxide); 3.07 (mc, 1H, epoxide); 3.42 (mc, 2H, CH$_2$Si); 5.15-5.65 (m, 3H); ppm.

C. [2S-(2α,3β,5α)]-2-Ethenyltetrahydro-5-methyl-2H-pyran-3-ol acetate 1. (2R-trans)-3-Ethenyl-β-methyloxiranepropanol To a solution of the title B compound (16.4 g, 64.1 mmol) in tetrahydrofuran (275 mL) was added tetrabutylammonium fluoride (87.5 mL, 96.2 mmol) and the mixture was stirred for one hour at room temperature. After addition of ether (600 mL) the solution was washed four times with water, dried and evaporated to give the crude title compound as a colorless oil (17.8 g). The product was used without further purification in the next step.

2. (2S-trans)-2-Ethenyltetrahydro-5-methyl-2H-pyran-3-ol

To a solution of the title 1 compound (17.8 g) in dichloromethane (500 mL) was added at −78° C., (+)-camphersulfonic acid (1.49 g, 6.41 mmol). The mixture was allowed to warm to room temperature within one hour and triethylamine (1.95 g, 19.2 mmol) was added. This solution of the title compound was used in the next step.

3. [2S-(2α,3β,5α)]-2-Ethenyltetrahydro-5-methyl-2H-pyran-3-ol acetate

To a solution of the title 2 compound were added at 0° C., acetic anhydride (9.82 g, 96.2 mmol), pyridine (10.1 g, 128.3 mmol) and dimethylaminopyridine (0.78 g). The mixture was stirred overnight at room temperature and then washed with saturated ammonium chloride solution. The organic phase was dried and evaporated to give the crude title compound (22.4 g) which was chromatographed on silica gel using petroleum ether/ether (93:7) as eluent. The compound containing fractions were collected and evaporated to give the title compound (0.63 g, 5.3%); and a mixture of isomers containing predominantly the title compound (3.44 g, 29.1%) as colorless oils.

IR (film): 1740 cm$^{-1}$ (CO)

$^1$H-NMR (CDCl$_3$ ): δ=0.97 (d, 3H); 1.70 (m, 2H); 1.99 (m, 1H); 2.00 (s, 3H); 3.53 (dd(AB), 1H; 11.3, 4.6 H$_2$); 3.61 (dd(AB), 1H; 11.3, 3.7 H$_2$); 3.89 (mc, 1H,); 4.87 (m, 1H); 5.25 (ddd, 1H; 10.6, 1.5, 1.5 H$_2$); 5.32 (ddd, 1H; 17.4, 1.5, 1.5 H$_2$); 5.79 (ddd, 1H; 17.4, 10.6, 5.8 H$_2$); ppm.

D. [2R-(2α,3β,5α)]-3-[[(1,1-Dimethylethyl)dimethylsilyloxy]tetrahydro-5-methyl-2H-pyran-2-carboxaldehyde 1. [2S-(2α,3β,5α)]-2-Ethenyltetrahydro-5-methyl-2H-pyran-3-ol To a solution of the title C compound (10.2 g, 55.4 mmol) in methanol (85 mL) was added a solution of potassium carbonate (7.65 g, 55.4 mmol) in water (85 mL) and the mixture was stirred overnight at room temperature. The solution was poured into ethyl acetate/water 2:1 (900 mL), and the phases were separated and the organic phase extracted twice with ethyl acetate. The combined organic phases were dried and evaporated to give the title compound as a colorless oil (7.4 g, 93.8%).

IR (film): 1640 (C=C), 3420 (OH) cm$^{-1}$ $^1$H-NMR (CDCl$_3$): δ=1.05 (d, 3H); 1.50–2.10 (m, 3H); 3.60 (mc, 4H); 5.20–5.50 (mc, 2H); 5.70–6.10 (mc, 1H); ppm.

2. [2S-(2α,3β,5α)-3-[[(1,1-Dimethylethyl)dimethylsilyl]oxy]-2-ethenyltetrahydro-5-methyl-2H-pyran To a solution of the title 1 compound (7.35 g, 51.7 mmol) in dimethylformamide (130 mL) were added tert-butyldimethylsilyl chloride (23.4 g, 155.0 mmol) and imidazole (10.9 g, 160.2 mmol). The mixture was stirred overnight at room temperature. After the addition of methanol (5 mL) and ether (500 mL) the solution was washed three times with water. The organic phase was dried and evaporated and the resulting crude product filtered over silica gel with ether/petroleum ether (1:9) as eluent and subsequently chromatographed on silica gel with 1% ether in petroleum ether to give the title compound as a colorless oil (10.2 g, 77.1%).

$^1$H-NMR (CDCl$_3$): δ=0.00 (s, 6H); 0.83 (s, 9H); 1.05 (d, 3H); 1.60–2.10 (m, 3H); 3.40–3.60 (m, 4H); 5.18 (ddd, 1H); 5.28 (ddd, 1H); 5.90 (ddd, 1H); ppm.

3. 2R-(2α,3β,5α)-3-[[(1,1-Dimethylethyl)dimethylsilyl]oxy]tetrahydro-5-methyl-2H-pyran-2-carboxaldehyde At −78° C., ozone was bubbled through a solution of the title 2 compound (5.13 g, 20.0 mmol) in dichloromethane (250 mL) until the solution turned violet. Excess of ozone was expelled with nitrogen and then a solution of triphenylphosphine (5.25 g, 20.0 mmol) in dichloromethane (50 mL) was added dropwise at −78° C. The mixture was then allowed to warm to room temperature and was stirred for 1.5 hours. The solvent was evaporated in vacuo and the residue chromatographed on silica gel (840 g) using petroleum ether/ether (1:3.5) as eluent. The sample containing fractions were collected and evaporated to give the title compound as a colorless oil (3.23 g, 62.5%).

IR (film): 1740 cm$^{-1}$ (CO)

$^1$H-NMR (CDCl$_2$): δ=0.02, 0.04 (2s, 6H); 0.85 (s, 9H); 0.93 (d, 3H); 1.45–1.75 (m, 2H); 2.05 (m, 1H); 3.48 (dd, 1H); 3.67 (dd, 1H); 4.03 (m, 1H); 9.80 (s, 1H); ppm.

E. [2R-(2α,3β,5α)]-1-[-3-[[(1,1-Dimethylethyl)dimethylsilyl]oxy]tetrahydro-5-methyl-2H-pyran-2-yl]ethanone 1. [2S-(2α,3β,5α)]-3-[[(1,1-Dimethylethyl)dimethylsilyl]oxy]-tetrahydro-o,5-dimethyl-2H-pyran-2-methanol To a solution of the title D compound (3.24 g, 12.5 mmol) in ether (150 mL) was added at 0° C. a 3M solution of methylmagnesium iodide in ether (6.3 mL, 18.8 mmol) and the mixture was stirred for 1.25 hours. The solution was washed with saturated ammonium chloride solution and the aqueous phase extracted twice with ether. The combined organic phases were washed successively with sodium hydrogen carbonate solution, water and brine and then dried. Evaporation of the solvent gave the crude title compound as a colorless oil (3.42 g, 99.5%).

IR (film): 3480 (OH) cm$^{-1}$ $^1$H-NMR (CDCl$_3$): δ=0.04, 0.06 (2s, 6H); 0.85 (s, 9H); 1.02 (2d, 3H); 1.18, 1.22 (2d, 3H); 1.50–2.00 (m, 3H); 2.80, 3.00 (2m, 1H); 3.45–3.65 (m, 2H); 3.65–4.0 (m, 2H); ppm.

2. [2R-(2α,3β,5α)]-1-[-3-[[(1,1-Dimethylethyl)-dimethylsilyl]oxy]tetrahydro-5-methyl-2H-pyran-2-yl]ethanone To a solution of the title 1 compound (3.42 g, 12.5 mmol) in dichloromethane (170 mL) was added molsieve 4A (34.2 g) and after five minutes stirring, pyridinium chlorochromate (10.74 g, 49.8 mmol). The mixture was stirred overnight at room temperature. The molsieve was filtered off, silica gel was added and the solvent distilled off in vacuo. The silica gel was added on top of a column containing silica gel (840 g) and the product eluted with petroleum ether/ether (2:1) as eluent to give the title compound as a colorless oil (2.40 g, 73.3%).

IR (film): 1725 (CO) cm$^{-1}$ $^1$H-NMR (CDCl$_3$): δ=0.00, 0.02 (2s, 6H); 0.85 (s, 9H); 0.95 (d, 3H); 1.50–1.75 (m, 2H); 2.05 (m, 1H); 2.22 (s, 3H); 3.37 (dd, 1H); 3.62 (dd, 1H); 3.71 (d, 1H); 4.05 (m, 1H); ppm.

F. [2S-(2α(E),3β,5α)]-3-[3-[[(1,1-Dimethylethyl)dimethylsilyl]oxy]tetrahydro-5-methyl-2H-pyran-2-yl]-2-butenenitrile To a solution of sodium hydride (329 mg, 11.0 mmol) in tetrahydrofuran (50 mL) was added dropwise at 0° C. a solution of diethyl cyanmethylphosphonate (1.94 g, 11.0 mmol) in dry tetrahydrofuran (50 mL). After stirring for one hour a solution of the title E compound (2.49 g, 9.1 mmol) in tetrahydrofuran (50 mL) was added dropwise. The mixture was allowed to warm to room temperature and was stirred for 2.5 hours. The mixture was then poured into icewater and extracted twice with ether. The combined organic phases were washed with brine, dried and evaporated. The residue was chromatographed on silica gel (280 g) using petroleum ether/ether (95:5) as eluent. Collection of the sample-containing fractions and evaporation of the solvent gave the title compound (2.59 g, 95.9%) as a colorless oil (E/Z-mixture 88:12).

IR (film): 2220 (CN) cm$^{-1}$ $^1$H-NMR (CDCl$_3$): δ= −0.05, −0.02 (2s, 6H); 0.82 (s, 9H); 1.07 (d, 3H); 1.50-2.0 (m, 3H); 1.90+2.05 (2d, 3H); 3.40-3.75+4.00 (m, 4H); 5.22+5.35 (2q, 1H); ppm.

G. [2S-(2α(E),3β,5α)]-3-[3-[[(1,1-Dimethylethyl)dimethylsilyl]oxy]tetrahydro-5-methyl-2H-pyran-2-yl]-2-butenal To a solution of the title F compound (2.59 g, 8.76 mmol) in toluene (250 mL) was added dropwise at 0° C. and under an argon atmosphere a 1M solution of diisobutylaluminium hydride in toluene (10.5 mL, 10.5 mmol). After stirring for two hours, a saturated ammonium chloride solution (100 mL) and after an additional five minutes 2N sulfuric acid (40 mL) was added dropwise. The phases were separated and the aqueous phase extracted twice with ether. The combined organic phases were washed with brine, dried and evaporated. The residue was chromatographed on silica gel (260 g) using petroleum ether/ether (95:5) as eluent. Collection of the sample-containing fractions and evaporation of the solvent gave the title compound (1.89 g, 72.3%) as a colorless oil (containing about 10% Z-isomer).

IR (film): 1680 (CHO) cm$^{-1}$ $^1$H-NMR (CDCl$_3$): β= −0.1, −0.02 (2s, 6H); 0.79 (s, 9H); 1.09 (2d, 3H); 1.65 (m, 1H); 1.75-2.0 (m, 2H); 1.96+2.18 (2d, 3H); 3.40-3.75+4.35 (m, 4H); 5.92+6.04 (2dq, 1H); 10.00+10.04 (2d, 1H); ppm.

H. [2S-(2α(E,E,E),3β,5α)]-3-[[(1,1-Dimethylethyl)dimethylsilyl]oxy]tetrahydro-5-methyl-2-(1-methyl-1,3,5-nonatrienyl)-2H-pyran A 1.6M solution of n-butyl lithium (3.05 mL, 4.44 mmol) in hexane was added dropwise at 10° C. to a sonicated suspension of 2-hexenyltriphenylphosphonium bromide (1.89 g, 4.44 mmol) in dry toluene (44 mL) under an argon atmosphere. After 15 minutes a solution of the title G compound (1.32 g, 4.44 mmol) in toluene (44 mL) was added to the homogeneous reaction mixture and the mixture was stirred for 15 minutes with sonication. The mixture was washed three times with a pH 3.5 buffer solution, dried and evaporated. The crude product was chromatographed on silica gel with ether/petroleum ether (5:95) to give a mixture of the (E,E,E)- and (E,E,E)-isomers (1.06 g, 65.7%). The isomers were partly separated with a second chromatography with a 1:99 ratio of the solvent mixture. Yield: 511 mg of the title compound, 331 mg of the (E,Z,E)-isomer and 333 mg of a mixture of the title compound and the (E,Z,E)-isomer.

$^1$H-NMR (CDCl$_3$): δ= −0.12, −0.07 (2s, 6H); 0.77 (s, 9H); 0.85 (t, 3H); 1.08 (d, 3H); 1.38 (m, 2H); 1.50-2.00 (m, 3H); 1.75 (d, 3H); 2.05 (q, 2H); 3.38 (d, 1H); 3.50-3.75 (m, 3H); 5.65 (m, 1H); 5.95-6.35 (m, 4H); ppm.

I. Glycine, [2S-[2α(E,E,E)3β,5α]]Tetrahydro-5-methyl-2-(1-methyl-1,3,5-nonatrienyl)-2H-pyran-3-yl ester 1. [2S-[2α,(E,E,E),3β,4α]]-Tetrahydro-5-methyl-2-(1-methyl-1,3,5-nonatrienyl)-2H-pyran-3-ol To a solution of the title H compound (255 mg, 0.70 mmol) in dry tetrahydrofuran (50 mL) was added tetrabutylammonium fluoride (3.17 mL, 3.50 mmol; 1.1M solution in tetrahydrofuran) and the mixture was stirred for two hours at room temperature. The solvent was distilled off and the residue taken up in ethyl acetate. The solution was washed with water and brine, dried and vaporated to give the crude title compound (194 mg) which was used in the next step without further purification.

IR (film): 3400 cm$^{-1}$ (OH, broad)

$^1$H-NMR (CDCl$_3$): δ=0.80 (m, 3H); 1.09 (d, 3H); 1.35 (m, 2H); 1.55 (m, 1H, burried under water); 1.77 (d, 3H); 1.85-2.10 (m, 4H); 3.37 (d, 1H); 3.45-3.75 (m, 3H); 5.70 (mc, 1H); 6.0-6.4 (m, 4H); ppm.

2. N-[[2-(Trimethylsilyl)ethoxy]carbonyl]glycine

To a solution of glycine (375 mg, 5.00 mmol) in water (5 mL) were added a solution of triethylamine (759 mg, 7.50 mmol) in dioxane (5 mL) and glycine (1.54 g, 5.5 mmol) and the mixture was stirred overnight at room temperature. The mixture was poured in water (50 mL) and the pH was brought from 4.7 to 2 with saturated potassium hydrogensulfate solution. The mixture was then extracted three times with ethyl acetate. The combined organic phases were washed four times with water, dried and evaporated to give the crude oily title compound (1.48 g) which still contained some hydroxybenztriazole. This oil was triturated with ether, filtered and evaporated to give the title compound (973 mg, 88.7%) as a colorless oil (contained traces of hydroxybenztriazole).

IR (film): 1725 (broad, CO) cm$^{-1}$ $^1$H-NMR (DMSO-d$_6$) δ= −0.05 (s, 9H); 0.89 (m, 2H); 3.55 (d, 2H); 4.04 (m, 2H); 7.30 (t, 1H); 12.60 (s, broad, 1H); ppm.

3. N-[[2-(Trimethylsilyl)ethoxy]carbonyl]glycine, [2S-[2α(E,E,E),3β,4α]]tetrahydro-5-methyl-2-(1-methyl-1,3,5-nonatrienyl)-2H-pyran-3-yl ester Under an argon atmosphere, the title 2 compound (613 mg, 2.80 mmol), ethyl-3-(3-dimethylamino)propyl carbodiimide (536 mg, 2.80 mmol) and dimethylamino pyridine (85 mg) were added to a solution of the crude title 1 compound (194 mg) in dichloromethane (110 mL). After stirring for one hour at room temperature the mixture was washed with degassed water, dried and evaporated after the addition of silica gel. The crude product adsorbed on silica gel was chromatographed on silica gel (80 g) using ether/petroleum ether (1:5) as eluent. The product-containing fractions were combined and evaporated to yield the title compound (227 mg, 71.9%).

IR (film): 1730, 1755 cm$^{-1}$ (CO) $^1$H-NMR (CDCl$_3$): δ= −0.02 (s, 9H); 0.90 (mc, 5H); 1.10 (d, 3H); 1.38 (m, 2H); 1.70 (m, 1H); 1.72 (s, 3H); 1.80-2.10 (m, 4H); 3.60 (mc, 3H); 3.65 (dd, AB, 1H); 3.92 (dd, AB, 1H); 4.10 (mc, 2H); 4.95 (m, 1H, NH); 5.05 (mc, 1H); 5.68 (mc, 1H); 5.90-6.35 (m, 4H); ppm.

4. Glycine, [2S-[2α(E,E,E)3β,5α]]Tetrahydro-5-methyl-2-(1-methyl-1,3,5-nonatrienyl)-2H-pyran-3-yl-ester Under an argon atmosphere the title 3 compound (223 mg, 0.49 mmol) was dissolved in tetrahydrofuran (5 mL) and tetrabutylammonium fluoride (1.12 mL, 1.23 mmol; 1.1M solution in tetrahydrofuran) was added. After stirring for 45 minutes at 40° C. the volatiles were distilled off in vacuo and the residue dissolved in ethyl acetate. The solution was washed twice with water and brine, dried and evaporated. The crude product was chromatographed on silica gel (45 g) using ethyl acetate/pentane (85:15) as eluent. The product-containing fractions were combined and evaporated to yield the title compound (104 mg; 68%). Prior to the evaporation a few crystals of butylated hydroxytoluene was added.

IR (film): 1740 cm$^{-1}$ (CO)

$^1$H-NMR (CDCl$_3$): $\delta$=0.87 (t, 3H); 1.10 (d, 3H); 1.38 (m, 2H); 1.70 (mc, 1H); 1.75 (d, 3H); 1.80-2.40 (m, 6H, contains NH$_2$ and water); 3.32 (d, AB, 1H); 3.37 (d, AB, 1H); 3.58 (mc, 3H); 5.08 (mc, 1H); 5.68 (mc, 1H); 5.90-6.35 (m, 4H); ppm.

EXAMPLE 2

Glycine, [2S-[2α(E,E,E),3β,5β]Tetrahydro-5-methyl-2-(1-methyl-1,3,5-nonatrienyl)-2H-pyran-3-yl ester A. [2S-(2α,3β,5β)]-2-Ethenyltetrahydro-5-methyl-2H-pyran-3-ol acetate 1. [2S-(2α,3β,5β)]-2-Ethenyltetrahydro-5-methyl-2H-pyran-3-ol acetate To a solution of (2S-trans)-2-ethenyltetrahydro-5-methyl-2H-pyran-3-ol (as prepared in Example I) was added acetic anhydride (9.82 g, 96.2 mmol), pyridine (10.1 g, 128.3 mmol) and dimethylaminopyridine (0.78 g) at 0° C. The mixture was stirred overnight at room temperature and then washed with saturated ammonium chloride solution. The organic phase was dried and evaporated to give the crude title compound (22.4 g) which was pchromatographed on silica gel using petroleum ether/ether (93:7) as eluent. The compound containing fractions were collected and evaporated to give the title compound (3.28 g, 17.8%), an isomer (0.63 g, 5.3%) and a mixture of both compounds containing predominantly the isomer (3.44 g, 29.1%) as colorless oils. IR (film): 1740 cm$^{-1}$ (CO)

$^1$H-NMR (CDCl$_3$): $\delta$=0.83 (d, 3H); 1.14 (ddd, 1H; 12.1, 12.1, 11.0 H$_2$); 1.87 (m, 1H); 2.15 (m, 1H); 2.00 (s, 3H); 3.00 (dd=t, 1H; 11.2, 11.2 Hz); 3.58 (dd, 1H; 9.5, 6.6 Hz); 3.86 (ddd, 1H; 11.2, 4.4, 1.9 Hz); 4.60 (ddd, 1H; 11.0, 9.5, 4.6 Hz); 5.19 (ddd, 1H; 10.4, 1.8, 0.9 Hz); 5.29 (ddd, 1H; 17.3, 1.8, 1.1 Hz); 5.78 (ddd, 1H; 17.3, 10.4, 6.6 Hz); ppm.

B. [2R-(2α,3β,5β)]-3-[[(1,1-Dimethylethyl)dimethylsilyl]oxy]tetrahydro-5-methyl-2H-pyran-2-carboxaldehyde 1. [2S-(2α,3β,5β)-2-Ethenyltetrahydro-5-methyl-2H-pyran-3-ol To a solution of the title A compound (8.6 g, 46.7 mmol) in methanol (70 mL) was added a solution of potassium carbonate (6.45 g, 46.7 mmol) in water (70 mL) and the mixture was stirred overnight at room temperature. The solution was poured into ethyl acetate/water (400 mL, 2:1), the phases were separated and the organic phase extracted twice with ethyl acetate. The combined organic phases were dried and evaporated to give the title compound (6.4 g, 95.8%) as a colorless oil.

IR (film): 1645 (C=C), 3420 (OH) cm$^{-1}$ $^1$H-NMR (CDCl$_3$): $\delta$=0.87 (d, 3H); 1.17 (m, 1H); 1.60-2.30 (m, 2H); 2.95 (dd=t, 1H); 3.40 (mc, 2H); 3.85 (mc, 1H); 5.20-5.50 (mc, 2H); 5.70-6.10 (mc, 1H); ppm.

2. [2S-(2α,3β,5β)]-3-[[(1,1-Dimethylethyl)dimethylsilyl]oxy]-2-ethenyltetrahydro-5-methyl-2H-pyran To a solution of the title 1 compound (6.36 g, 44.8 mmol) in dimethylformamide (120 mL) were added tert-butyldimethylsilyl chloride (13.5 g, 89.5 mmol) and imidazole (6.1 g, 89.5 mmol). The mixture was stirred overnight at room temperature and 1 equivalent each of tert-butyldimethylsilyl chloride and of imidazole was added. After stirring for two days methanol (8 mL) and ether (150 mL) was added and the solution was washed three times with water. The organic phase was dried and evaporated and the resulting crude product filtered over silica gel with ether/petroleum ether (1:9) as eluent to give the title compound (11.9 g, quant.) as a colorless liquid.

$^1$H-NMR (CDCl$_3$): $\delta$=0.00, 0.02 (2s, 6H); 0.85 (m, 12H); 1.13 (mc, 1H); 1.80 (mc, 1H); 1.98 (mc, 1H); 2.96 (dd=t, 1H); 3.35 (mc, 2H); 3.82 (mc, 1H); 5.18 (ddd, 1H); 5.28 (ddd, 1H); 5.88 (ddd, 1H); ppm.

3. [2R-(2α,3β,5β)]-3-[[(1,1-Dimethylethyl)dimethylsilyl]oxy]tetrahydro-5-methyl-2H-pyran-2-carboxaldehyde At −78° C., ozone was bubbled through a solution of the title 2 compound (0.51 g, 2.0 mmol) in dichloromethane (30 mL) until the solution turned violet. Excess of ozone was expelled with nitrogen and then a solution of triphenylphosphine (0.52 g, 2.0 mmol) in dichloromethane (10 mL) was added dropwise at −78° C. The mixture was then allowed to warm to room temperature and was stirred for 1.5 hours. The solvent was evaporated in vacuo and the residue chromatographed on silica gel (80 g) using petroleum ether/ether (1:3) as eluent. The sample containing fractions were collected and evaporated to give the title compound (0.41 g, 79.4%) as a colorless oil.

IR (film): 1740 cm$^{-1}$ (CO)

$^1$H-NMR (CDCl$_3$): $\delta$=0.00, 0.05 (2s, 6H); 0.85 (m, 12H); 1.20 (mc, 1H); 1.80 (mc, 1H); 2.05 (mc, 1H); 2.94 (dd=t, 1H); 3.65 (mc, 2H); 3.87 (mc, 1H); 9.78 (s, 1H); ppm.

C. [2R-(2α,3β,5β)]-1-[-3-[[(1,1-Dimethylethyl)dimethylsilyl]oxy]tetrahydro-5-methyl-2H-pyran-2-yl]ethanone 1. [2S-(2α,3β,5β)]-3-[[(1,1-Dimethylethyl)dimethylsilyl]-oxy]tetrahydro-α,5-dimethyl-2H-pyran-2-methanol To a solution of the title B compound (4.07 g, 15.7 mmol) in ether (100 mL) was added a 3M solution of methylmagnesium iodide in ether (10.5 mL, 31.5 mmol) at 0° C. and the mixture was stirred for 1.5 hours. The solution was washed with saturated ammonium chloride solution and the aqueous phase extracted twice with ether. The combined organic phases were washed successively with sodium hydrogen carbonate solution, water and brine and then dried. Evaporation of the solvent gave the crude title compound (3.61 g, 83.5%) as a colorless oil.

IR (film): 3480 (OH) cm$^{-1}$ $^1$H-NMR (CDCl$_3$): $\delta$=0.04, 0.06 (2s, 6H); 0.80 (d, 3H); 0.85 (s, 9H); 1.10 (m, 1H); 1.12, 1.20 (2d, 3H); ca. 1.70 (m, 1H) (burried under water); 1.97 (m, 1H); 2.70-3.00 (m, 2H); 3.40-4.0 (m, 3H); ppm.

2. [2R-(2α,3β,5β)]-1-[[1,1-Dimethylethyl)dimethylsilyl]oxy]tetrahydro-5-methyl-2H-pyran-2-yl]ethanol To a solution of the title 1 compound 3.61 g, 13.1 mmol) in dichloromethane (180 mL) was added molsieve 4A (36.1 g) and after five minutes stirring, pyridinium chlorochromate (11.34 g, 52.6 mmol). The mixture was stirred overnight at room temperature. The molsieve was filtered off, silica gel was added and the solvent distilled off in vacuo. The silica gel was added on top of a column containing silica gel (230 g) and the product eluted with petroleum ether/ether (2:1) as eluent to give the title compound (3.59 g, 100%) as a colorless oil.

IR (film): 1730 (CO) cm$^{-1}$ $^1$H-NMR (CDCl$_3$): δ= −0.02, 0.01 (2s, 6H); 0.83 (m, 12H); 1.15 (m, 1H); 1.82 (m, 1H); 2.01 (m, 1H); 2.20 (s, 3H); 2.91 (dd=t, 1H); 3.50–3.70 (m, 2H); 3.81 (m, 1H); ppm.

D. [2S-(2α(E),3β,5β)]-3-[-3-[[(1,1-Dimethylethyl)dimethylsilyl]oxy]tetrahydro-5-methyl-2H-pyran-2-yl]-2-butenenitrile To a solution of sodium hydride (474 mg, 15.8 mmol) in tetrahydrofuran (70 mL) was added dropwise at 0° C. a solution of diethyl cyanmethylphosphonate (2.80 g, 15.8 mmol) in dry tetrahydrofuran (70 mL). After stirring for one hour a solution of the title C compound (3.59 g, 13.2 mmol) in tetrahydrofuran (70 mL) was added dropwise. The mixture was allowed to warm to room temperature and was stirred for 1.5 hours. The mixture was then poured into icewater and extracted twice with ether. The combined organic phases were washed with brine, dried and evaporated. The residue was chromatographed on silica gel (280 g) using petroleum ether/ether (95:5) as eluent. Collection of the sample-containing fractions and evaporation of the solvent gave the title compound (2.63 g, 67.4%) as a colorless oil (E/Z-mixture 88:12).

IR (film): 2220 (CN) cm$^{-1}$ $^1$H-NMR (CDCl$_3$): δ= −0.05, 0.00 (2s, 6H); 0.82 (m, 12H); 1.20 (m, 1H); 1.80 (m, 2H); 2.01 (m, 1H); 1.88+2.04 (2d, 3H); 2.93+3.00 (2dd=2t, 1H); 3.30–3.55+4.00 (m, 3H); 3.80 (m, 1H); 1.88+2.04 (2d, 3H); 2.93+3.00 (2dd=2t, 1H); 3.30–3.55+4.00 (m, 3H,); 3.80 (m, 1H); 5.23+5.33 (2q, 1H); ppm.

E. [2S-(2α(E),3β,5α)]-3-[-3-[[(1,1-Dimethylethyl)dimethylsilyl]oxy]tetrahydro-5-methyl-2H-pyran-2 TM yl]-2-butenal To solution of the title D compound (2.63 g, 8.90 mmol) in toluene (250 mL) was added dropwise at 0° C. and under an argon atmosphere a 1M solution of diisobutylaluminium hydride in toluene (10.7 mL, 10.7 mmol). After stirring for two hours a saturated ammonium chloride solution (100 mL) and after an additional five minutes, 2N sulfuric acid (40 mL) was added dropwise. The phases were separated and the aqueous phase extracted twice with ether. The combined organic phases were washed with brine, dried and evaporated. The residue was chromatographed on silica gel (260 g) using petroleum ether/ether (96:4, up to 93:7) as eluent. Collection of the sample-containing fractions and evaporation of the solvent gave the title compound (2.17 g, 81.5%) as a colorless oil (contained about 17% Z-isomer).

IR (film): 1680 (CHO) cm$^{-1}$ $^1$H-NMR (CDCl$_3$): δ= −0.12, −0.03 (2s, 6H); 0.85 (m, 12H); ca. 1.1 (m, 1H); 1.75 (m, 1H); 2.00 (m, 1H); 1.91+2.14 (2d, 3H); 2.92+2.95 (2dd=2t, 1H); 3.45–4.35 (m, 3H); 3.80 (m, 1H); 5.92+6.00 (2dq, 1H); 9.98+10.01 (2d, 1H); ppm.

F. [2S-(2α(E,E,E),3β,5β)]-3-[[(1,1-Dimethylethyl)-dimethylsilyl]oxy]tetrahydro-5-methyl-2-(1-methyl-1,3,5-nonatrienyl)-2H-pyran A 1.6M solution of n-butyl lithium (5.00 mL, 7.50 mmol) in hexane was added dropwise at 10° C. to phosphonium bromide (3.09 g, 7.27 mmol) in dry toluene (72 mL) under an argon atmosphere. After 15 minutes, a solution of the title E compound (2.17 g, 7.27 mmol) in toluene (72 mL) was added dropwise to the homogeneous reaction mixture and the mixture was stirred for 15 minutes with sonication. The mixture was washed three times with a pH 3.5 buffer solution, dried and evaporated. The crude product was chromatographed on silica gel with ether/petroleum ether (5:95) to give a mixture of the (E,E,E)- and (E,Z,E)-isomers (1.59 g, 59.9%). The isomers were partly separated with a second chromatography with a 1:99 ratio of the solvent mixture. Yield: 205 mg of the title compound, 494 mg of the (E,Z,E)-isomer and 882 mg of a mixture of the title compound and the (E,Z,E)-isomer. A further chromatography of the mixture furnished 353 mg of the title compound and 426 mg of a mixture of the isomers.

$^1$H-NMR (CDCl$_3$): δ= −0.12, −0.05 (2s, 6H); 0.75–0.90 (m, 15H); 0.87 (t, 3H); 1.15 (m, 1H); 1.38 (m, 2H); 1.72 (d, 3H); 1.75 (m, 1H); 2.05 (m, 3H); 2.93 (dd=t, 1H); 3.30–3.50 (m, 2H); 3.78 (m, 1H); 5.65 (m, 1H); 5.95–6.50 (m, 4H); ppm.

G. Glycine, [2S-[2α(E,E,E),3β,5β]]Tetrahydro-5-methyl-2-(1-methyl-1,3,5-nonatrienyl)-2H-pyran-3-yl ester 1. [2S-2α(E,E,E),3β,4β]]-Tetrahydro-5-methyl-2-(1-methyl-1,3,5-nonatrienyl)-2H-pyran-3-ol To a solution of the title F compound (353 mg, 0.97 mmol) in dry tetrahydrofuran (70 mL) was added tetrabutylammonium fluoride (4.40 mL, 4.84 mmol: 1.1M solution in tetrahydrofuran) and the mixture was stirred for 2.5 hours at room temperature. The solvent was distilled off and the residue taken up in ethyl acetate. The solution was washed with water and brine, dried and evaporated to give the crude title compound (267 mg) which was used in the next step without further purification.

2. N-[[2-(Trimethylsilyl)ethoxy]carbonyl]glycine, 2S-2α(E,E,E),3β,4β]]-tetrahydro-5-methyl-2-(1-methyl-1,3,5-nonatrienyl)-2H-pyran-3-yl ester Under an argon atmosphere, N-[[2-(trimethylsilyl)ethoxy]carbonyl]glycine (as prepared in Example 1; 849 mg, 3.87 mmol), ethyl-3-(3-dimethyl-amino)propyl carbodiimide (742 mg, 3.87 mmol) and dimethylamino pyridine (118 mg) was added to a solution of crude title 1 compound (267 mg) in dichloromethane (150 mL). After stirring for one hour at room temperature the mixture was washed with degassed water, dried and evaporated after the addition of silica gel. The crude product adsorbed on silica gel was chromatographed on silica gel using ether/petroleum ether (1:5) as eluent. The product-containing fractions were combined and evaporated to yield 402 mg of the title compound (91.9%).

IR (film): 1730, 1755 cm$^{-1}$ (CO)

$^1$H-NMR (CDCl$_3$): δ= −0.03 (s, 9H); 0.85 (mc, 8H); 1.15 (m, 1H); 1.35 (m, 2H); 1.68 (d, 3H); 1.75–2.20 (m, 4H); 2.97 (t, 3H); 3.49 (d, 1H); 3.67 (dd, 1H); 3.75–4.00 (m, 1H); 4.10 (mc, 2H); 4.80 (m, 1H); 4.93 (mc, 1H, NH); 5.70 (mc, 1H); 5.90–6.35 (m, 4H); ppm.

3. Glycine, [2S-[2α(E,E,E),3β,5β]]-Tetrahydro-5-methyl-2-(1-methyl-1,3,5-nonatrienyl)-2H-pyran-3-yl ester Under an argon atmosphere the title 2 compound (290 mg, 0.64 mmol) was dissolved in tetrahydrofuran (7 mL) and tetrabutylammonium fluoride (1.46 mL, 1.60 mmol; 1.1M solution in tetrahydrofuran) was added. After stirring for 1.25 hours at 40° C. the volatiles were distilled off in vacuo and the residue dissolved in ethyl acetate. The solution was washed twice with degassed water and brine, dried and evaporated. The crude product was chromatographed on silica gel (45 g) using ethyl acetate/pentane (85:15) as eluent. The product-containing fractions were combined and evaporated to yield a total of 164 mg of the title compound (80.6%). (Prior to the evaporation a few crystals of butylated hydroxytoluene were added).

IR (film): 1750 cm$^{-1}$ (CO)

$^1$H-NMR (CDCl$_3$):δ=0.87 (mc, 5H); 1.22 (m, 1H); 1.38 (m, 2H); 1.70 (d, 1H); 1.80–2.40 (m, 6H, contains NH$_2$, burried under water); 3.00 (t, 1H); 3.40 (d, 1H); 3.51 (2d, 2AB, 2H); 3.85 (m, 1H); 4.82 (m, 1H); 5.70 (mc, 1H); 5.90–6.35 (m, 4H); ppm.

EXAMPLE 3

Glycine, [2S-[2α(E,Z,E),3β,5α]]Tetrahydro-5-methyl-2-(1-methyl-1,3,5-nonatrienyl)-2H-pyran-3-yl ester A. 2S-[2α(E,Z,E),3β,5α]-3-[[(Dimethylethyl)dimethylsilyl]oxy]tetrahydro-5-methyl-2-(1-methyl-1,3,5-nonatrienyl)-2H-pyran A 1.6M solution of n-butyl lithium (3.05 mL, 4.44 mmol) in hexane was added dropwise at 10° C. to a sonicated suspension of 2-hexenyltriphenylphosphonium bromide (1.89 g, 4.44 mmol) in dry toluene (44 mL) under an argon atmosphere. After 15 minutes a solution of the title G compound of Example 1 (1.32 g, 4.44 mmol) in toluene (44 mL) was added dropwise to the homogeneous reaction mixture and the mixture was stirred for 15 minutes with sonication. The mixture was washed three times with a pH 3.5 buffer solution, dried and evaporated. The crude product was chromatographed on silica gel with ether/petroleum ether (5:95) to give a mixture of the (E,E,E)- and (E,Z,E)-isomers (1.06 g, 65.7%). The isomers were partly separated with a second chromatography with a 1:99 ratio of the solvent mixture. Yield: 511 mg of the E,E,E isomer, 331 mg of the title compound and 333 mg of a mixture of isomers.

$^1$H-NMR (CDCl$_3$): δ= −0.12, −0.06 (2s, 6H); 0.77 (s, 9H); 0.87 (t, 3H); 1.40 (d, 3H); 1.38 (m, 2H); 1.50–2.00 (m, 3H); 1.75 (d, 3H); 2.05 (q, 2H); 3.45 (d, 1H); 3.50–3.75 (m, 3H); 5.67 (dt, 1H); 5.92 (t, 1H); 6.05 (t, 1H); 6.40–6.55 (m, 2H); ppm.

B. [2S-[2α(E,Z,E),3β,4α]]-Tetrahydro-5-methyl-2-(1-methyl-1,3,5-nonatrienyl)-2H-pyran-3-ol To a solution of the title A compound (331 mg, 0.91 mmol) in dry tetrahydrofuran (65 mL) was added tetrabutylammonium fluoride (4.13 mL, 4.54 mmol; 1.1M solution in tetrahydrofuran) and the mixture was stirred for two hours at room temperature. The solvent was distilled off and the residue taken up in ethyl acetate. The solution was washed with water and brine, dried and evaporated to give the crude product (215 mg) which was used in the next step without further purification.

IR (film):3420 cm$^{-1}$ (OH, broad).

C. N-[[2-(Trimethylsilyl)ethoxy]carbonyl]glycine, [2S-[2α(E,Z,E),3β,4β]]tetrahydro-5-methyl-2-(1-methyl-1,3,5-nonatrienyl)-2H-pyran-3-yl ester Under an argon atmosphere the title I.2. compound of Example 1 (752 mg, 3.43 mmol), ethyl-3-(3-dimethylamino)propyl carbodiimide 658 mg, 3.43 mmol) and dimethylamino pyridine (85 mg) were added to a solution of crude title B compound (215 mg) in dichloromethane (110 mL). After stirring for one hour at room temperature the mixture was washed with degassed water and evaporated after the addition of silica gel. The crude product adsorbed on silica gel was chromatographed on silica gel (80 g) using ether/petroleum ether (1:5) as eluent. The product-containing fractions were combined and evaporated to yield 323 mg of the title compound (83.3%).

IR (film):1725, 1755 cm$^{-1}$ (CO)

$^1$H-NMR (CDCl$_3$): δ= −0.02 (s, 9H); 0.89 (mc, 5H); 1.11 (d, 3H); 1.38 (m, 2H); 1.70 (m, 1H); 1.74 (d, 3H); 1.80–2.10 (m, 4H); 3.60 (mc, 3H); 3.68 (dd, AB, 1H); 3.93 (dd, AB, 1H); 4.10 (mc, 2H); 4.93 (m, 1H, NH); 5.08 (mc, 1H); 5.71 (mc, 1H); 5.88–6.07 (m, 2H); 6.35–6.55 (m, 2H), ppm.

D. Glycine, [2S-[2α(E,Z,E),3β,5α]]Tetrahydro-5-methyl-2-(1,3,5-nonatrienyl)-2H-pyran-3-yl ester Under an argon atmosphere the title C compound (323 mg, 0.71 mmol) was dissolved in tetrahydrofuran (8 mL) and tetrabutylammonium fluoride (1.63 mL, 1.79 mmol; 1.1M solution in tetrahydrofuran) was added. After stirring for 50 minutes at 40° C. the volatiles were distilled off in vacuo and the residue dissolved in ethyl acetate. The solution was washed twice with degassed water and brine, dried and evaporated. The crude product was chromatographed on silica gel (80 g) using ethyl acetate/pentane (85:15) as eluent. The product-containing fractions were combined and evaporated to yield a total of 162 mg (73.7%) of the title compound. (Prior to the evaporation a few crystals of butylated hydroxytoluene was added).

IR (film): 1740 cm$^{-1}$ (CO)

−$^1$H-NMR (CDCl$_3$): δ=0.88 (t, 3H); 1.12 (d, 3H); 1.38 (m, 2H); 1.70 (mc, 1H); 1.75 (d, 3H); 1.80–2.20 (m, 6H, contains NH$_2$ and water); 3.28 (d, AB, 1H); 3.35 (d, AB, 1H); 3.61 (mc, 3H); 5.10 (mc, 1H); 5.73 (mc, 1H); 5.88 (mc, 2H); 6.3–6.55 (m, 2H); ppm.

EXAMPLE 4

Glycine, [2S-[2α(E,Z,E),3β,5β]]Tetrahydro-5-methyl-2-(1-methyl-1,3,5-nonatrienyl)-2H-pyran-3-yl ester A. [2S-[2α(E,Z,E),3β,5β]-3-[[(1,1-Dimethylethyl)dimethylsilyl]oxy]tetrahydro-5-methyl-2-(1-methyl-1,3,5-nonatrienyl)-2H-pyran A 1.6M solution of n-butyl lithium (5.00 mL, 7.50 mmol) in hexane was added dropwise at 10° C. to a sonicated suspension of 2-hexenyltriphenylphosphonium bromide (3.09 g, 7.27 mmol) in dry toluene (72 mL) under an argon atmosphere. After 15 minutes a solution of the title E compound of Example 2 (2.17 g, 7.27 mmol) in toluene (72 mL) was added dropwise to the homogeneous reaction mixture and the mixture was stirred for 15 minutes with sonication. The mixture was washed three times with a pH 3.5 buffer solution, dried and evaporated. The crude product was chromatographed on silica gel with ether/petroleum ether (5:95) to give a mixture of the (E,E,E)- and (E,Z,E)-isomers (1.59 g, 59.9%). The isomers were partly separated with a second chromatography with a 1:99 ratio of the solvent mixture. Yield: 205 mg of the E,E,E isomer, 494 mg of the title compound and 882 mg of a mixture of the isomers.

¹H-NMR (CDCl₃): δ= −0.12, −0.04 (2s, 6H); 0.75–0.90 (m, 15H); 1.15 (m, 1H); 1.38 (m, 2H); 1.72 (d, 3H); 1.75 (m, 1H); 2.05 (m, 3H); 2.95 (dd=t, 1H); 3.45 (m, 2H); 3.80 (m, 1H); 5.67 (dt, 1H); 5.92 (t, 1H); 6.04 (t, 1H); 6.40–6.55 (m, 2H); ppm.

B. [2S-[2α(E,Z,E),3β,4β]]-Tetrahydro-5-methyl-2-(1-methyl-1,3,5-nonatrienyl)-2H-pyran-3-ol To a solution of the title A compound (494 mg, 1.35 mmol) in dry tetrahydrofuran (50 mL) was added tetrabutylammonium fluoride (6.16 mL, 6.77 mmol; 1.1M solution in tetrahydrofuran) and the mixture was stirred for 2.25 hours at room temperature. The solvent was distilled off and the residue taken up in ethyl acetate. The solution was washed with water and brine, dried and evaporated to give the crude title product (428 mg) which was used in the next step without further purification.

IR (film):3400 cm⁻¹ (OH, broad)

¹H-NMR (CDCl₃): δ= −0.87 (mc, 6H); 1.10 (mc, 1H); 1.40 (mc, 2H); 1.78 (d, 3H); 1.80 (m, 1H); 2.00–2.25 (m, 3H); 2.97 (t, 1H); 3.40 (d, 1H); 3.45 (mc, 2H); 5.72 (mc, 1H); 6.05 (mc, 2H); 6.4–6.6 (mc, 2H); ppm.

C. N-[[2-Trimethylsilyl)ethoxy]carbonyl]glycine, [2S-[2α(E,Z,E),3β,4β]]-tetrahydro-5-methyl-2-(1-methyl-1,3,5-nonatrienyl)-2H-pyran-3-yl ester Under an argon atmosphere the title I.2 compound of Example 1 (1.19 g, 5.42 mmol), ethyl-3-(3-dimethylamino)propyl carbodiimide (1.03 g, 5.42 mmol) and dimethylamino pyridine (260 mg) were added to a solution of the crude title B compound (428 mg) in dichloromethane (210 mL). After stirring for one hour at room temperature the mixture was washed with degassed water, dried and evaporated after the addition of silica gel. The crude product adsorbed on silica gel was chromatographed on silica gel (80 g) using ether/petroleum ether (1:5) as eluent. The product-containing fractions were combined and evaporated to yield 564 mg (73.0%) of the title compound.

IR (film):1720, 1755 cm⁻¹ (CO)

¹H-NMR (CDCl₃): δ= −0.02 (s, 9H); 0.90 (mc, 8H); 1.10 (mc, 1H); 1.39 (mc, 2H); 1.70 (d, 3H); 1.87 (mc, 1H); 2.00–2.25 (m, 3H); 3.00 (t, 1H); 3.55 (d, 1H); 3.65 (dd, AB, 1H); 3.85 (mc, 2H); 4.10 (mc, 2H); 4.75–5.00 (m, 2H); 5.70 (mc, 1H); 5.95 (mc, 2H); 6.40–6.55 (m, 2H); ppm.

D. Glycine, [2S-[2α(E,Z,E),3β,5β]]Tetrahydro-5-methyl-2-(1-methyl-1,3,5-nonatrienyl)-2H-pyran-3-yl ester Under an argon atmosphere the title C compound (564 mg, 1.25 mmol) was dissolved in tetrahydrofuran (12 mL) and tetrabutylammonium fluoride (2.84 mL, 3.12 mmol; 1.1M solution in tetrahydrofuran) was added. After stirring for 1.25 hours at 40° C. the volatiles were distilled off in vacuo and the residue dissolved in ethyl acetate. The solution was washed twice with water and brine, dried and evaporated. The crude product was chromatographed on 80 g silica gel using ethyl acetate/pentane 85:15 as eluent. The product-containing fractions were combined and evaporated to yield 112 mg of the title compound. Prior to the evaporation of the fractions a few crystals of 2,6-di-tert-butyl-4-methylphenol were added.

IR (film):1750 cm⁻¹ (CO) ¹H-NMR (CDCl₃): δ=0.82 (mc, 6H); 1.20 (mc, 1H); 1.38 (mc, 2H); 1.72 (d, 1H); ca. 1.85 (mc, 1H, burried under water); 2.00–2.25 (m, 5H, contains NH₂); 3.00 (t, 1H); 3.25+3.30 (2d, 2AB, 2H); 3.56 (d, 1H); 3.85 (mc, 1H); 4.82 (mc, 1H); 5.71 (mc, 1H); 5.98 (mc, 2H); 6.30–6.55 (m, 2H); ppm.

EXAMPLE 5

Glycine, 2S-[2α(E,E,E),3β,5α]-Tetrahydro-5-methyl-2-(1,3,5-nonatrienyl)-2H-pyran-3-yl ester A. [2S-[2α(E,E,E),3β,5α]]-3-[[(1,1-Dimethylethyl)-dimethylsilyl]oxy]tetrahydro-5-methyl-2-(1,3,5-nonatrienyl)-2H-pyran A 1.6M solution of n-butyl lithium (2.75 mL, 4.40 mmol) in hexane was added dropwise at 10° C. to a sonicated suspension of 2,4-octadienyltriphenylphosphonium bromide (1.99 g, 4.40 mmol) in dry toluene (40 mL) under an argon atmosphere. After 15 minutes a solution of the title D compound of Example 1 (1.03 g, 4.0 mmol) in toluene (40 mL) was added dropwise to the homogeneous reaction mixture and the mixture was stirred for 15 minutes with sonication. The mixture was washed three times with a pH 3.5 buffer solution, dried and evaporated. The crude product was chromatographed on silica gel with ether/petroleum ether (3:97) as eluent. The product-containing fractions were combined and evaporated to yield 720 mg (62.1%) of a mixture (ca. 7:2) of the (E,E,E)- and the (Z,E,E,)-isomer of the title compound.

B. 2S-[2α(E,E,E),3β,5α]]-Tetrahydro-5-methyl-2-(1,3,5-nonatrienyl)-2H-pyran-3-ol To a solution of the title A compond (720 mg, 2.05 mmol) in dry tetrahydrofuran (40 mL) was added tetrabutylammonium fluoride (9.32 mL, 10.3 mmol; 1.1M solution in tetrahydrofuran) and the mixture was stirred for one hour at room temperature. The solvent was distilled off and the residue taken up in ethyl acetate. The solution was washed with water and brine, dried and evaporated after the addition of silica gel. The crude product adsorbed on silica gel was chromatographed on silica gel (230 g) using ether/petroleum ether (1:3) as eluent. The product-containing fractions were combined and evaporated to yield 391 mg (80.7%) of pure title compound besides some fractions containing minor amounts of the (Z,E,E)-isomer of title compound.

IR (film):3400 cm⁻¹ (OH, broad)

¹H-NMR (CDCl₃): δ=0.85 (m, 3H); 1.02 (d, 3H); 1.35 (m, 2H); 1.60 (m, 1H, buried under water); 1.77 (d, 3H); 1.75–2.10 (m, 4H); 3.50–3.65 (m, 3H); 5.55–5.75 (m, 2H); 5.95–6.4 (m, 4H); ppm.

C. [2S-[2α(E,E,E),3β,5α)]-N-[2-Trimethylsilyl)ethoxy]carbonylglycine, tetrahydro-5-methyl-2-(1,3,5-nonatrienyl)-2H-pyran-3-yl ester Under an argon atmosphere TEOC-glycine the title I.2. compound of Example 1 (543 mg, 2.47 mmol), ethyl-3-(3-dimethyl-amino)propyl carbodiimide (473 mg, 2.47 mmol) and dimethylamino pyridine (200 mg) were added to a solution of the title B compound (391 mg, 1.65 mmol) in dichloromethane (60 mL). After stirring for one hour at room temperature the mixture was washed three times with degassed water, dried and evaporated after the addition of silica gel. The crude product adsorbed on silica gel was chromatographed on silica gel (130 g) using ether/petroleum ether (1:4) as eluent. The product-containing fractions were combined and evaporated to yield 354 mg (47.9%) of the title compound.

IR (film):1730, 1750 cm⁻¹ (CO).

D. Glycine, [2S-[2α(E,E,E),3β,5α]]-Tetrahydro-5-methyl-2-(1,3,5-nonatrienyl)-2H-pyran-3-yl ester Under an argon atmosphere the title C compound (153 mg, 0.35 mmol) was dissolved in tetrahydrofuran (10 mL) and tetrabutylammonium fluoride (0.80 mL, 0.88 mmol; 1.1M solution in tetrahydrofuran) was added. After stirring for 45 minutes at 40° C. the volatiles were distilled off in vacuo and the residue dissolved in ethyl acetate. The solution was washed four times with degassed water, dried and evaporated. The crude product was chromatographed on silica gel (45 g) using ethyl acetate/pentane 85:15 as eluent. The product-containing fractions were combined and evaporated to yield 43 mg (41.9%) of the title compound as a pale yellow oil. Prior to the evaporation a few crystals of 2,6-di-tert-butyl-4-methylphenol were added.

IR (film): 1740 cm$^{-1}$ (CO)

$^1$H-NMR (CDCl$_3$): δ=0.87 (t, 3H); 0.98 (d, 3H); 1.38 (m, 2H); 1.72 (mc, 1H); 1.80–2.20 (m, 6H, contains NH$_2$ and water); 3.37 (s, 2H); 3.53 (mc, 2H); 3.92 (t, 1H); 4.87 (q, 1H); 5.50–5.80 (m, 2H); 5.95–6.35 (m, 4H); ppm.

EXAMPLE 6

Glycine, [2S-[2α(E,E,E),3β,5β]]-Tetrahydro-5-methyl-2-(1,3,5-nonatrienyl)-2H-pyran-3-yl ester A. [2S-[2α(E,E,E),3β,5β]]-3-[[(1,1-Dimethylethyl)-dimethylsilyl]oxy]tetrahydro-5-methyl-2-(1,3,5-nonatrienyl)-2H-pyran 2.75 mL (4.40 mmol) of a 1.6M solution of n-butyl lithium in hexane was added dropwise at 10° C. to a sonicated suspension of 2,4-octadienyltriphenylphosphonium bromide (1.99 g, 4.40 mmol) in dry toluene (40 mL) under an argon atmosphere. After 15 minutes a solution of the title B compound of Example 2 (1.03 g, 4.0 mmol) in toluene (40 mL) was added dropwise to the homogeneous reaction mixture and the mixture was stirred for 15 minutes with sonication. The mixture was washed three times with a pH 3.5 buffer solution, dried and evaporated. The crude product was chromatographed on silica gel with ether/petroleum ether 3:97 as eluent. The product-containing fractions (41–43 and 44–80) were combined and evaporated to yield the title B compound (99 mg, 7.1%) containing 90.9% the (E,E,E)-isomer (fraction 1) and 993 mg (66.5%) of a mixture (ca. 5:1) of the (E,E,E)- and the (Z,E,E)-isomer (fraction 2).

B. [2S-[2α(E,E,E),3β,5β]]-Tetrahydro-5-methyl-2-(1,3,5-nonatrienyl)-2H-pyran-3-ol To a solution of the title A compound (857 mg, 2.44 mmol) in dry tetrahydrofuran (50 mL) were added 11.1 mL (12.2 mmol) tetrabutylammonium fluoride (1.1M solution in tetrahydrofuran) and the mixture was stirred for one hour at room temperature. The solvent was distilled off and the residue taken up in ethyl acetate. The solution was washed with water and brine, dried and evaporated after the addition of silica gel. The crude product adsorbed on silica gel was chromatographed on silica gel (260 g) using ether/petroleum ether 1:1 as eluent. The product-containing fractions (41–47, 48–54 and 55–62) were combined and evaporated to yield 201 mg (34.8%) of pure title compound (fraction 1), 248 mg of a mixture (2:7) of the title compound and the (Z,E,E)-isomer of the title compound (fraction 2) and 76 mg of a 4:5-mixture of these isomers (fraction 3). The title compound solidified on standing.

IR (film): 3400 cm$^{-1}$ (OH)

$^1$H-NMR (CDCl$_3$): δ=0.83 (mc, 6H); 1.06 (ddd, 1H); 1.35 (m, 2H); 1.80 (mc, 1H); 1.95–2.20 (m, 3H); 2.94 (t, 1H); 3.25–3.45 (m, 2H); 3.81 (m, 1H); 5.50–5.80 (m, 2H); 5.95–6.4 (m, 4H); ppm.

C. [2S-[2α(E,E,E),3β,5β]]-N-[[2-(Trimethylsilyl)ethoxycarbonylglycine, tetrahydro-5-methyl-2-(1,3,5-nonatrienyl)-2H-pyran-3-yl ester Under an argon atmosphere TEOC-glycine (the title I.2. compound of Example 1; 373 mg, 1.70 mmol), ethyl-3-(3-dimethyl-amino)propyl carbodiimide (336 mg, 1.70 mmol) and 104 mg dimethylamino pyridine were added to a solution of the title B compound (201 mg, 0.85 mmol) in dichloromethane (20 mL). After stirring for two hours at room temperature the mixture was washed three times with degassed water, dried and evaporated after the addition of silica gel. The crude product adsorbed on silica gel was chromatographed on silica gel (45 g) using ether/petroleum ether 1:4 as eluent. The product-containing fractions were combined and evaporated to yield 353 mg (94.8%) of the title compound. The title compound solidified on standing.

IR (film): 1740, 1775 cm$^{-1}$ (CO) $^1$H-NMR (CDCl$_3$): δ=−0.01 (s, 9H); 0.83 (mc, 6H); 0.94 (mc, 2H); 1.15 (ddd, 1H); 1.35 (m, 2H); 1.85 (mc, 1H); 1.95–2.25 (m, 3H); 2.98 (t, 1H); 3.55–4.00 (m, 4H); 4.12 (mc, 2H); 4.62 (mc, 1H); 5.50 (dd, 1H); 5.65 (m, 1H); 5.95–6.35 (m, 4H); ppm.

D. Glycine, [2S-[2α(E,E,E),3β,5β]]-Tetrahydro-5-methyl-2-(1,3,5-nonatrienyl)-2H-pyran-3-yl ester Under argon atmosphere the title C compound (150 mg, 0.34 mmol) was dissolved in tetrahydrofuran (10 mL) and 0.78 mL (0.86 mmol) tetrabutylammonium fluoride (1.1M solution in tetrahydrofuran) were added. After stirring for one hour at 40° C. the volatiles were distilled off in vacuo and the residue dissolved in ethyl acetate. The solution was washed four times with degassed water and twice with brine, dried and evaporated. The crude product was chromatographed on silica gel (45 g) using ethyl acetate/pentane 95:5 as eluent. The product-containing fractions were combined and evaporated to yield 75 mg (74.5%) of the title compound as pale yellow solid (Prior to the evaporation a few crystals of 2,6-di-tert-butyl-4-methylphenol (butylated hydroxytoluene) were added).

IR (film): 1735 cm$^{-1}$ (CO)

$^1$H-NMR (CDCl$_3$): δ=0.85 (mc, 6H); 1.17 (m, 1H); 1.38 (m, 2H); 1.80–2.20 (m, 4H); 3.00 (t, 1H); 3.47 (2AB, 2H); 3.62 (m, 1H); 3.82 (m, 1H); 4.62 (m, 1H); 5.51 (dd, 1H); 5.66 (mc, 1H); 5.95–6.35 (m, 4H); ppm.

EXAMPLE 7

Glycine, [2S-(2α,3β,5β)]-tetrahydro-5-methyl-2-nonyl-2H-pyran-3-yl ester

A. [2S-[2α,3β,5β)-N-[[2-(Trimethylsilyl)ethoxy]carbonyl]glycine, tetrahydro-5-methyl-2-nonyl-2H-pyran-3-yl ester A stream of hydrogen was bubbled for one hour through a solution of the title C compound of Example 6 (200 mg, 0.457 mmol) in methanol (10 mL) containing palladium (40 mg) on activated carbon (10%). Excess hydrogen was replaced with nitrogen and the catalyst was filtered off with suction. The filtrate was evaporated to yield the crude title compound which was chromatographed on silica gel (45 g) using ether/pentane 1:4 as eluent. The product-containing fraction were combined and evaporated to yield the title compound as an oil (163 mg, 80.4%).

IR (film): 1730, 1755 cm$^{-1}$ (CO)

$^1$H-NMR (CDCl$_3$): δ=0.00 (s, 9H); 0.82 (m, 6H); 0.97 (m, 2H); 1.11 (m, 1H); 1.23 (s, 16H); 1.80 (mc, 1H); 2.15 (m, 1H); 2.91 (t, 1H); 3.10 (m, 1H); 3.80 (mc, 1H); 3.91 (mc, 2H); 4.15 (mc, 2H); 4.55 (mc, 1H); 5.01 (s, broad, 1H); ppm.

B.  Glycine, [2S-(2α,3β,5β)]-tetrahydro-5-methyl-2-nonyl-2H-pyran-3-yl ester

Under an argon atmosphere the title A compound (153 mg, 0.35 mmol) was dissolved in tetrahydrofuran (10 mL) containing 0.80 mL (0.88 mmol) tetrabutylammonium fluoride (1.1M solution in tetrahydrofuran, predried with 4A molsieve). After stirring for one hour at room temperature the volatiles were distilled off in vacuo and the residue dissolved in ethyl acetate. The solution was washed four times with degassed water, dried and evaporated. The crude product was chromatographed on silica gel (45 g) using ethyl acetate/pentane 95:5 as eluent. The product-containing fractions were combined and evaporated to yield the title compound (91 mg, 82.6%) as pale yellow oil (Prior to the evaporation a few crystals of 2,6-di-tert-butyl-4-methylphenol (butylated hydroxytoluene) were added).

IR (film): 1740 cm$^{-1}$ (CO)

$^1$H-NMR (CDCl$_3$): δ=0.81 (m, 6H); 1.07 (m, 1H); 1.23 (s, 16H); 1.82 (mc, 1H); 2.15 (mc, 1H); 2.91 (t, 1H); 3.09 (m, 1H); 3.39 (s, 2H); 3.80 (mc, 1H); 4.52 (mc, 1H); ppm.

EXAMPLE 8

Glycine, [2S-(2α,3β,5β)]-tetrahydro-5-methyl-2-nonyl-2H-pyran-3-yl ester

A.  [2S-(2α,3β,5α)]-N-[[(2-Trimethylsilyl)ethoxy]carbonyl]glycine, tetrahydro-5-methyl-2-nonyl-2H-pyran-3-yl ester A stream of hydrogen was bubbled for one hour through a solution of the title C compound of Example 5 (157 mg, 0.359 mmol) in methanol (10 mL) containing palladium (31 mg) on activated carbon (10%). Excess hydrogen was replaced with nitrogen and the catalyst was filtered off with suction. The filtrate was evaporated to yield the crude title compound which was chromatographed on silica gel (45 g) using ether/pentane 1:4 as eluent. The product-containing fractions were combined and evaporated to yield the title compound as an oil (126 mg, 79.1%).

IR (film) 1725, 1755 cm$^{-1}$ (CO)

$^1$H-NMR (CDCl$_3$): δ=0.00 (s, 9H); 0.75-1.15 (m, 8H); 1.23 (s, 16H); 1.65-2.10 (m, 3H); 3.33 (m, 1H); 3.51 (d, 2H); 3.92 (d, 2H); 4.15 (mc, 2H); 4.79 (mc, 1H); 5.05 (s, broad, 1H); ppm.

B.  Glycine, [2S-(2α,3β,5β)]-tetrahydro-5-methyl-2-nonyl-2H-pyran-3-yl ester

Under an argon atmosphere the title A compound (125 mg, 0.28 mmol) was dissolved in tetrahydrofuran (10 mL) containing 0.64 mL (0.71 mmol) tetrabutylammonium fluoride (1.1M solution in tetrahydrofuran, predried with 4A molsieve). After stirring for one hour at room temperature, the volatiles were distilled off in vacuo and the residue dissolved in ethyl acetate. The solution was washed four times with degassed water, dried and evaporated. The crude product was chromatographed on silica gel (45 g) using ethyl acetate/pentane 95:5 as eluent. The product-containing fractions were combined and evaporated to yield the title compound as an oil (47 mg, 55.1%).

IR (film): 1740 cm$^{-1}$ (CO)

$^1$H-NMR (CDCl$_3$): δ=0.83 (t, 3H); 0.98 (d, 3H); 1.22 (s, 15H); 1.45 (m, 2H); 1.6-1.8 (m, 2H); 2.00 (NH$_2$ and water); 3.25-3.60 (m, 5H); 4.77 (mc, 1H); ppm.

EXAMPLE 9

Glycine, [2S-[2α(1E,3Z,5E),3β]-Tetrahydro-2-(1-methyl-1,3,5-nonatrienyl)-2H-pyran-3-yl ester A.  (2S-trans)-3-(Acetyloxy)-3,6-dihydro-2H-pyran-2-methanol,acetate To a solution of 1,2-dideoxy-3,4,6-tri-O-acetyl-S-arabino-1-hexenopyranose (12.8 g, 0.047 mol) in dichloromethane (50 mL) was added triethylsilane (6.56 g, 0.056 mol) and the mixture cooled to 0° C. Boron trifluoride etherate (6.7 g, 0.047 mol) was added and the reaction mixture stirred for 45 minutes at 0° C. The mixture was diluted with saturated aqueous sodium bicarbonate (100 mL) and with ether (500 mL) and the organic layer separated. It was washed twice with water, once with brine, dried over sodium sulfate, and evaporated in vacuo. Yield: 9.8 g (97%) oil.

B.  (2S-trans)-3,6-Dihydro-3-hydroxy-2H-pyran-2-methanol

To a solution of the title A compound (9.8 g, 0.0457 mol) in dry methanol (80 mL) was added sodium methylate (45.7 mL of a 1M solution in methanol) and the mixture stirred for two hours at room temperature. Dry ice (15 g) was added and the mixture stirred for ten minutes at room temperature. The solvent was evaporated in vacuo and the residue triturated with ethyl acetate. The unsoluble salts were filtered off by suction, and the organic layer was evaporated in vacuo. Yield: 5.6 g (95%) oil.

C.  (2S-trans)-Tetrahydro-3-hydroxy-2H-pyran-2-methanol

To a solution of the title B compound (5.6 g, 0.043 mol) in dry methanol (50 mL) was added palladium on carbon (0.5 g, 10%) and hydrogen bubbled through for three hours. The catalyst was filtered off by suction over Hyflo and the solvent evaporated in vacuo. Yield: 5.0 g (88%) oil.

D.  (2S-trans)-3-[[(1,1-Dimethylethyl) dimethylsilyl]oxy]-2-[[[(1,1-dimethylethyl)dimethylsilyl]oxy]methyl]-tetrahydro-2H-pyran To a solution of the title C compound (5.0 g, 37.8 mmol) and imidazole (6.4 g, 94.6 mmol) in dimethylformamide (50 mL) was cooled to 0° C. and t-butyldimethylchlorosilane (12.5 g, 83 mmol) added. The mixture was stirred for two hours at room temperature and methanol (6.5 mL) added. After ten minutes, the mixture was diluted with ether and the organic layer separated and washed twice with water. The water was re-extracted twice with ether, and the combined organic layers were washed again with water and with brine. The organic solution was dried over sodium sulfate and evaporated in vacuo. Yield: 12.7 g (93%) oil.

E.  (2S-trans)-3-[[(1,1-Dimethylethyl) dimethylsilyl]oxy]tetrahydro-2H-pyran-2-methanol To an ice-cold solution of the title D compound (27.3 g, 76 mmol) in tetrahydrofuran (82 mL) and water (82 mL) was added trifluoroacetic acid (75.8 mL) and the mixture stirred for one hour at 0° C. The pH was adjusted to 6.3 by the addition of 2N sodium hydroxide and the reaction mixture extracted twice with ether.

The combined organic layers were washed with water, dried over sodium sulfate, and evaporated in vacuo. The residue was purified by column chromatography on silica gel using ether/petroleum ether (1:1) as eluent. Yield: 7.7 g (41%) oil.

F. (2S-trans)-3-[(1,1-Dimethylethyl) dimethylsilyloxy]-tetrahydro-α-methyl-2H-pyran-2-methanol A solution of oxalylchloride (19.8 g, 0.156 mol) in dichloromethane (380 mL) was cooled to −60° C. and a solution of dimethyl sulfoxide (17.1 g, 0.228 mol) in dichloromethane (70 mL) added dropwise. After stirring for 30 minutes, a solution of the title E compound (12.9 g, 52 mmol) in dichloromethane (100 mL) was added dropwise and the mixture stirred for four hours at between −30° C. and −40° C. The reaction mixture was again cooled to −60° C., triethylamine (52.6 g, 0.52 mmol) added and stirred for one hour at 0° C. The solution was poured into ether (300 mL) and the unsoluble material filtered off by suction. The filtrate was evaporated in vacuo and the resulting residue dissolved in ether (300 mL). This solution was cooled to −20° C, methylmagnesium iodide (91 mL, 0.273 mol) in ether (50 mL) added dropwise, and stirred for one hour at 0° C. The mixture was cooled to −60° C., saturated aqueous ammonium chloride (5 mL) added dropwise, and poured into saturated aqueous ammonium chloride (300 mL). This solution was extracted several times with ethyl acetate, and the combined organic layers were dried over sodium sulfate and evaporated in vacuo. The residue was purified by column chromatography on silica gel using ether/petroleum ether (1:1) as eluent. Yield: 7.39 g (55%) of isomer 1 as an oil and 2.36 g (17%) of isomer 2 as an oil. Total yield: 72%.

G. (2R-trans)-1-[3-[[(1,1-Dimethylethyl) dimethylsilyloxy]tetrahydro-2H-pyran-2-yl]ethanone To a solution of the title F compound (8.6 g, 33 mmol) in dichloromethane (150 mL) was added molecular sieve (4 A, 56 g) and pyridinium chlorochromate (28.4 g, 132 mmol) and the mixture stirred for five hours at room temperature. After filtration over silica gel (elution with dichloromethane), the filtrate was evaporated in vacuo and the residue purified by column chromatography on silica gel using ether/petroleum (1:1) ether as eluent. Yield: 5.85 g (69%) oil.

H. 2S-[2α(E),3β]]-3-[3-[[(1,1-Dimethylethyl)dimethylsilyl]oxy]tetrahydro-2H-pyran-2-yl]-2-butenenitrile To an ice-cold solution of sodium hydride (12.5 g, 80% in oil, 0.416 mol) in dry tetrahydrofuran (200 mL) was added dropwise a solution of cyanomethyl diethylphosphonate (8.86 g, 0.05 mol) in dry tetrahydrofuran (100 mL). After stirring for 20 minutes at 0° C., a solution of the title G compound (10.77 g, 0.041 mol) in dry tetrahydrofuran (200 mL) was added dropwise within one hour, and the mixture was stirred for another 90 minutes at 0° C. After the dropwise addition of brine (200 mL), the reaction mixture was extracted three times with ether. The combined organic layers were dried over sodium sulfate and evaporated in vacuo. The residue was purified by column chromatography on silicagel using ether/petroleum ether (1:2) as eluent. Yield: 8.12 g (68%) oil.

I. [2S-[2α(E),3β]]-3-[3-[(1,1-Dimethylethyl)dimethylsilyl]oxy]tetrahydro-2H-pyran-2-yl]-2-butenal A solution of the title H compound (8.12 g, 0.028 mol) in dry toluene (300 mL) was cooled to 10° C. and diisobutylaluminumhydride (43 mL of a 1M solution in toluene, 0.043 mol) added dropwise. After stirring for one hour at room temperature, the mixture was again cooled to 10° C. and saturated aqueous ammonium chloride (100 mL) added dropwise, followed by the dropwise addition of 2N sulfuric acid (130 mL). The reaction mixture was extracted several times with ether, and the combined organic layers were dried over sodium sulfate and evaporated in vacuo. The residue was purified by column chromatography on silicagel using ether/petroleum ether (1:1) as eluent. Yield: 3.69 g (51%) oil.

J. [2S-[2α(E,Z,E),3β]]-3-[3-[(1,1-Dimethylethyl)dimethylsilyl]oxy]tetrahydro-2-(1-methyl-1,3,5-nonatrienyl)-2H-pyran A suspension of trans-2-hexenyl triphenylphosphonium bromide (6.0 g, 14.1 mmol) in dry toluene (70 mL) was cooled to 10° C. and n-butyllithium (10 mL, 1.6M solution in toluene, 15.9 mmol) added dropwise. Under sonication a solution of the title I compound (1.8 g, 6.3 mmol) in toluene (70 mL) was added dropwise and the reaction mixture stirred another 15 minutes under sonication. The solution was washed three times with pH 3.5 buffer, dried over sodium sulfate, and evaporated in vacuo. The residue was purified by column chromatography on silicagel using pentane/ethyl acetate (9:1) as eluent, to obtain a mixture of isomers. Yield: 1.58 g (63%) oil. The mixture of isomers (1.58 g) were separated by column chromatography on silicagel using petroleum ether with increasing amounts of ether (0→1%) as eluent.

Yield: 0.316 g (13%) title compound; H.I.=97.2% (by HPLC) and 0.533 g (21%) E,E,E,-isomer (=compound A of Example 10); H.I.=96.4% (by HPLC)

K. [2S-[2α(E,Z,E),3β]]-Tetrahydro-2-(1-methyl-1,3,5-nonatrienyl)-2H-pyran-3-ol

To a solution of the title J compound (0.30 g, 0.86 mmol) in dry tetrahydrofuran was added tetrabutylammonium fluoride (1.1M in tetrahydrofuran, 3.9 mL, 4.27 mmol), and the mixture was stirred for two hours at room temperature. The solvent was evaporated in vacuo and the residue dissolved in ethyl acetate. The organic solution was washed four times with water, and the combined water washings were reextracted with ethyl acetate. The combined organic layers were dried over sodium sulfate, and the solvent was evaporated in vacuo. Yield: 0.26 g (>quant.) oil.

L. N-[[2-(Trimethylsily)ethoxy]carbonyl]glycine, [2S-[2α(E,Z,E),3β]]-tetrahydro-2-(1-methyl-1,3,5-nonatrienyl)-2H-pyran-3-yl ester To a solution of crude title K compound (0.26 g, 0.85 mmol) in dry dichloromethane (150 mL) was added N-(trimethylsilylethoxy)carbonylglycine (0.72 g, 3.3 mmol), ethyl-3-(3-dimethylamino)propylcarbodiimide hydrochloride (0.63 g, 3.3 mmol), 4-dimethylaminopyridine (0.13 g, 1 mmol), and a trace of 2,6-di-tert-butyl-4-methylphenol. The mixture was stirred for one hour at room temperature and washed three times with water. The water was reextracted with dichloromethane, and the combined organic layers were dried over sodium sulfate and evaporated in vacuo. The residue was purified twice by column chromatography on silicagel using ethyl acetate containing 15% pentane as eluent. Yield: 0.245 g (56%) oil.

M. Glycine, [2S-[2α(1E,3Z,5E),3β]-Tetrahydro-2-(1-methyl-1,3,5-nonatrienyl)-2H-pyran-3-yl ester To a solution of the title L compound (0.24 g, 0.71 mmol) in dry tetrahydrofuran (5 mL) was added tetrabutylammonium fluoride (1.2 mL, 1.1M solution in tetrahydrofuran, 1.37 mmol) and the mixture stirred for 90 minutes at 40° C. The solvent was evaporated in vacuo and the residue dissolved in ethyl acetate. The organic solution was washed three times with water, and the water was reextracted with ethyl acetate. The combined organic layers were washed with brine, dried over sodium sulfate, and evaporated in vacuo. The residue was purified by column chromatography on silicagel using ethyl acetate containing 15% pentane as eluent.

Yield: 0.021 g (13%) oil; HPLC:H.I.=91.8% 0.059 g (37%) oil; HPLC:H.I.=94.1% 0.032 g (21%) oil; HPLC:H.I.=82.0%

Total yield: 71%

EXAMPLE 10

Glycine, [2S-[2α(E,E,E),3β]-Tetrahydro-2-(1-methyl-1,3,5-nonatrienyl)-2H-pyran-3-yl ester A. [2S-2α(E,E,E),3β]-3-[3-[[(1,1-Dimethylethyl)dimethylsilyl]oxy]tetrahydro]-2-(1-methyl-1,3,5-nonatrienyl)-2H-pyran A suspension of trans-2-hexenyl triphenylphosphonium bromide (6.0 g, 14.1 mmol) in dry toluene (70 mL) was cooled to 10° C. and n-butyllithium (10 mL, 1.6M solution in toluene, 15.9 mmol) added dropwise. Under irridiation with ultrasound a solution of the title I compound of Example 9 (1.8 g, 6.3 mmol) in toluene (70 mL) was added dropwise and the reaction mixture stirred another 15 minutes in the ultrasound bath. The solution was washed three times with pH 3.5 buffer, dried over sodium sulfate, and evaporated in vacuo. The residue was purified by column chromatography on silicagel using pentane/ethyl acetate (9:1) as eluent to obtain a mixture of isomers. Yield: 1.58 g (63%) oil. The mixture of isomers (1.58 g) was separated by column chromatography on silicagel using petroleum ether with increasing amounts of ether (0→1%) as eluent. Yield: 0.533 g (21%) title compound; H.I.=96.4% (by HPLC) and 0.326 g (13%) of the E,Z,E,-isomer (=compound J of Example 9).

B. [2S-[2α(E,E,E),3β]]-Tetrahydro-2-(1-methyl-1,3,5-nonatrienyl)-2H-pyran-3-ol

To a solution of the title A compound (0.30 g, 0.86 mmol) in dry tetrahydrofuran was added tetrabutylammonium fluoride (1.1M in tetrahydrofuran, 3.9 mL, 4.27 mmol), and the mixture was stirred for two hours at room temperature. The solvent was evaporated in vacuo and the residue dissolved in ethyl acetate. The organic solution was washed four times with water, and the combined water washings were reextracted with ethyl acetate. The combined organic layers were dried over sodium sulfate, and the solvent was evaporated in vacuo. Yield: 0.29 g (>quant.) oil.

C. N-[[2-(Trimethylsilyl)ethoxy]carbonyl]glycine, [2S-[2α(E,E,E),3β]]-tetrahydro-2-(1-methyl-1,3,5-nonatrienyl)-2H-pyran-3-yl ester To a solution of crude title B compound (0.29 g, 0.86 mmol) in dry dichloromethane (150 mL) was added N-(trimethylsilylethoxy)carbonylglycine (0.56 g, 2.6 mmol), ethyl-3-(3-dimethylamino)propylcarbodiimide hydrochloride (0.49 g, 2.6 mmol), 4-dimethylaminopyridine (0.13 g, 1 mmol), and a trace of 2,6-di-tert-butyl-4-methylphenol. The mixture was stirred for one hour at room temperature and washed three times with water. The water was reextracted with dichloromethane, and the combined orgnic layers were dried over sodium sulfate and evaporated in vacuo. The residue was purified by column chromatography on silicagel using ethyl acetate containing 15% pentane as eluent. Yield: 0.319 g (85%) oil.

D. Glycine, [2S-[2α(1E,3Z,5E),3β]]-Tetrahydro-2-(1-methyl-1,3,5-nonatrienyl)-2H-pyran-3-yl ester To a solution of the title C compound (0.31 g, 0.71 mmol) in dry tetrahydrofuran (5 mL) was added tetrabutylammonium fluoride (1.6 mL, 1.1M solution in tetrahydrofuran, 1.77 mmol) and the mixture stirred for 90 minutes at 40° C. The solvent was evaporated in vacuo and the residue dissolved in ethyl acetate. The organic solution was washed three times with water, and the water was reextracted with ethyl acetate. The combined organic layers were washed with brine, dried over sodium sulfate, and evaporated in vacuo. The residue was purified by column chromatography on silicagel using ethyl acetate containing 15% pentane as eluent.

Yield: 0.050 g (24%) oil; HPLC:H.I.=83.0% 0.108 g (52%) oil; HPLC:H.I.=93.4% 0.019 g ( 9%) oil; HPLC:H.I.=90.4%

Total yield: 86%.

EXAMPLE 11

Glycine, (2S-trans)-tetrahydro-2-(1-methylnonyl)-2H-pyran-3-yl ester

A. (2S-trans)-3-[[(1,1-Dimethylethyl)dimethylsilyl]oxy]tetrahydro-2-(1-methylnonyl)-2H-pyran A solution of the title A compound of Example 10 (0.14 g, 0.4 mmol) in methanol (20 mL) containing palladium on charcoal (10%, 0.02 g) was hydrogenated for 45 minutes at room temperature. The catalyst was filtered off by suction over Hyflo and the filtrate evaporated in vacuo. The residue was purified by column chromatography on silica gel using petroleumether/ether (9:1) as eluent.

Yield: 0.068 g (48%) oil.

B. (2S-trans)-Tetrahydro-2-(1-methylnonyl)-2H-pyran-3-ol

To a solution of the title A compound (0.066 g, 0.185 mmol) in dry tetrahydrofuran (10 mL) was added tetrabutylammonium fluoride (1.1M in tetrahydrofuran; 0.84 mL, 0.92 mmol), and the mixture was stirred for two hours at room temperature. The solvent was evaporated in vacuo and the residue dissolved in ethyl acetate. The organic solution was washed four times with water, and the combined water washings were reextracted with ethyl acetate. The combined organic layers were dried over sodium sulfate, and the solvent was evaporated in vacuo. This material was used without further purification for the subsequent reaction.

Yield: 0.05 g (>quant.) oil.

C. N-[[2-(Trimethylsilyl)ethoxy]carbonyl]glycine, (2S-trans)-tetrahydro-2-(1-methylnonyl)-2H-pyran-3-yl ester To a solution of crude title B compound (0.051 g, 0.185 mmol) in dry dichloromethane (10 mL) was added N-(trimethylsilylethoxy)carbonylglycine (0.12 g, 0.56 mmol), ethyl-3-(3-dimethylamino)propylcarbodiimide hydrochloride (0.11 g, 0.56 mmol), dimethylaminopropylamine (0.03 g, 0.23 mmol), and a trace of 2,6-di-tert-butyl-4-methylphenol. The mixture was stirred for one hour at room temperature and washed three times with water. The water was reextracted with dichloromethane, and the combined organic layers were dried over sodium sulfate and evaporated in vacuo. The residue was purified by column chromatography on silica gel using ether/petroleumether (1:1) as eluent.

Yield: 0.05 g (61%) oil.

D. Glycine, (2S-trans)-tetrahydro-2-(1-methylnonyl)-2H-pyran-3-yl ester

To a solution of the title C compound (0.05 g, 0.11 mmol) in dry tetrahydrofuran (5 mL) was added tetrabutylammonium fluoride (0.26 mL, 1.1M solution in tetrahydrofuran; 0.28 mmol) and the mixture stirred for 90 minutes at 40° C. The solvent was evaporated in vacuo and the residue dissolved in ethylacetate. The organic solution was washed three times with water, and the water was reextracted with ethyl acetate. The combined organic layers were washed with brine, dried over sodium sulfate, and evaporated in vacuo. The residue was purified twice by column chromatography on silica gel using ethyl acetate as eluent.

Yield: 0.016 g (49%) oil.

EXAMPLE 12

Glycine, [2S-[2α(E,E,E),3β]]-tetrahydro-2-[1-methyl-6-[2-naphthalenyl]-1,3,5-hexatrienyl-2H-pyran-3-yl ester A. [2S-[2α(E,E),3β]]-5-[3-[[(1,1-Dimethylethyl)dimethylsilyl]oxy]tetrahydro-2H-pyran-2-yl]-2,4-hexadiene-1-nitrile To an ice-cold solution of sodiumhydride (1.07 g, 80% in oil; 35.6 mmol) in dry tetrahydrofuran (35 mL) was added dropwise a solution of cyanomethyl diethylphosphonate (0.76 g, 4.27 mmol) in dry tetrahydrofuran (35 mL). After stirring for 20 minutes at 0° C., a solution of the title I compound of Example 9 (1.0 g, 3.56 mmol) in dry tetrahydrofuran (130 mL) was added dropwise within one hour, and the mixture was stirred for another 90 minutes at 0° C. After the dropwise addition of brine (40 mL), the reaction mixture was extracted three times with ether. The combined organic layers were dried over sodium sulfate and evaporated in vacuo. The residue was purified by column chromatography on silica gel using pentane/ether (9:1) ether as eluent.

Yield: 0.60 g (55%) oil.

B. [2S-[2α(E,E),3β]]-5-[3-[[(1,1-Dimethylethyl)dimethylsilyl]oxy]tetrahydro-2H-pyran-2-yl]-2,4-hexadiene-1-al A solution of the title A compound (0.60 g, 1.95 mmol) in dry toluene (30 mL) was cooled to 10° C. and diisobutylaluminumhydride (2.9 mL of a 1M solution in toluene, 2.9 mmol) added dropwise. After stirring for two hours at room temperature, another 1.5 mL of the diisobutylaluminumhydride solution was added and the mixture stirred for another hour. Saturated aqueous ammonium chloride (10 mL) was added dropwise, followed by the dropwise addition of 2N sulfuric acid (13 mL). The reaction mixture was extracted several times with ether, and the combined organic layers were dried over sodium sulfate and evaporated in vacuo. The residue was purified by column chromatography on silica gel using pentane/ether (2:1) as eluent.

Yield: 0.274 g (45%) oil.

C. [2S-[2α(E,E,E),3β]]-3-[[(1,1-Dimethylethyl)dimethylsilyl]oxy]tetrahydro-2-[1-methyl-6-(2-naphthalenyl)-1,3,5-heptatrienyl]-2H-pyran A suspension of (2-Naphthalenylmethyl)triphenylphosphonium bromide (0.53 g, 1.1 mmol) in dry toluene (15 mL) was cooled to 10° C. and n-butyllithium (0.69 mL, 1.6M solution in toluene; 1.1 mmol) added dropwise. Under sonication, a solution of the title B compound (0.31 g, 1.0 mmol) in toluene (15 mL) was added dropwise and the reaction mixture stirred another 15 minutes under sonication. The solution was washed three times with pH 3.5 buffer, dried over sodium sulfate, and evaporated in vacuo. The residue was purified by column chromatography on silica gel using pentane/ether (9:1) as eluent.

Yield: 0.152 g (35%) oil.

D. [2S-[2α-(E,E,E),3β]]-Tetrahydro-2-[1-methyl-6-(2-naphthalenyl)-1,3,5-heptatrienyl]-2H-pyran-3-ol To a solution of the title C compound (0.15 g, 0.345 mmol) in dry tetrahydrofuran (20 mL) was added tetrabutylammonium fluoride (1.1M in tetrahydrofuran; 1.6 mL, 1.7 mmol), and the mixture was stirred for two hours at room temperature. The solvent was evaporated in vacuo and the residue dissolved in ethyl acetate. The organic solution was washed four times with water, and the combined water washings were reextracted with ethyl acetate. The combined organic layers were dried over sodium sulfate, and the solvent was evaporated in vacuo.

Yield: 0.172 g (>quant.) oil. This material was used without further purification for the subsequent reaction.

E. N-[[2-(Trimethylsilyl)ethoxy]carbonyl]glycine, [2S-[2α(E,E,E),3β]]-tetrahydro-2-(1-methyl-6-(2-naphthalenyl)-1,3,5-hexatrienyl]-2H-pyran-3-yl ester To a solution of crude title D compound (0.172 g, 0.345 mmol) in dry dichloromethane (20 mL) was added N-(trimethylsilylethoxy)carbonylglycine (0.23 g, 1.04 mmol), ethyl-3-(3-dimethylamino)propylcarbodiimide hydrochloride (0.20 g, 1.04 mmol), 4-dimethylaminopyridine (0.05 g, 0.43 mmol), and a trace of 2,6-di-tert-butyl-4-methylphenol. The mixture was stirred for one hour at room temperature and washed three times with water. The water was reextracted with dichloromethane, and the combined organic layers were dried over sodium sulfate and evaporated in vacuo. The residue was purified by column chromatography on silica gel using ether containing 33% pentane as eluent.

Yield: 0.118 g (66%) oil.

F. Glycine, [2S-[2α(E,E,E),3β]]-tetrahydro-2-[1-methyl-6-[2-naphthalenyl]-1,3,5-hexatrienyl]-2H-pyran-3-yl ester To a solution of the title E compound (0.10 g, 0.19 mmol) in dry tetrahydrofuran (5 mL) was added tetrabutylammonium fluoride (0.43 mL, 1.1M solution in tetrahydrofuran; 0.48 mmol) and the mixture stirred for 90 minutes at 40° C. The solvent was evaporated in vacuo and the residue disolved in ethylacetate. The organic solution was washed three times with water, and the water was reextracted with ethyl acetate. The combined organic layers were washed with brine, dried over soidum sulfate, and evaporated in vacuo. The residue was purified by column chromatography on silica gel using ethyl acetate as eluent.

Yield: 0.048 g (67%) oil.

EXAMPLE 13

Glycine, [2S-[2α(E,E,E),3β]]-tetrahydro-2-(1-methyl-6-[3-(trifluoromethyl)phenyl]-1,3,5-hexatrienyl]-2H-pyran-3-yl ester A. [2S-[2α(E,E),3β]]-5-[3-[[(1,1-Dimethylethyl)dimethylsilyl]oxy]tetrahydro-2H-pyran-2-yl]-2,4-hexadiene-1-al A solution of the title A compound of Example 12 (0.60 g, 1.95 mmol) in dry toluene (30 mL) was cooled to 10° C. and diisobutylaluminumhydride (2.9 mL of a 1M solution in toluene, 2.9 mmol) added dropwise. After stirring for two hours at room temperature, another diisobutylaluminumhydride solution (1.5 mL) was added and the mixture stirred for another hour. Saturated aqueous ammonium chloride (10 mL) was added dropwise, followed by the dropwise addition of 2N sulfuric acid (13 mL). The reaction mixture was extracted several times with ether, and the combined organic layers were dried over sodium sulfate and evaporated in vacuo. The residue was purified by column chromatography on silica gel using pentane/ether (2:1) as eluent. Yield: 0.274 g (45%) oil.

B. [2S-[2α(E,E,E),3β]]-3-[[(1,1-Dimethylethyl)dimethylsilyl]oxytetrahydro-2-[1-methyl-6-[3-(trifluoromethyl)phenyl]-1,3,5-hexatrienyl]-2H-pyran 1. 3-Trifluoromethyl-benzyltriphenylphosphonium bromide A solution of 3-trifluoromethylbenzylbromide (4.6 g, 0.019 mol) and triphenylphosphine (5.0 g, 0.019 mol) in dry toluene (200 mL) was heated to reflux for two hours. The precipitate was filtered off by suction, washed with toluene, and dried in vacuo.

Yield: 6.77 g (71%); m.p. 289°-292° C.

2. [2S-[2α(E,E,E),3β]]-3-[[(1,1-Dimethylethyl)dimethylsilyl]oxy]tetrahydro-2-[1-methyl-6-[3-(trifluoromethyl)phenyl]-1,3,5-hexatrienyl]-2H-pyran A suspension of the title 1 compound (0.48 g, 0.96 mmol) in dry toluene (15 mL) was cooled to 10° C. and n-butyllithium (0.6 mL, 1.6M solution in toluene; 0.96 mmol) added dropwise. Under sonication, a solution of the title A compound (0.27 g, 0.87 mmol) in toluene (15 mL) was added dropwise and the reaction mixture stirred another 15 minutes under sonication. The solution was washed three times with pH 3.5 buffer, dried over sodium sulfate, and evaporated in vacuo. The residue was purified twice by column chromatography on silica gel using pentane/ether (9:1) as eluent.

Yield: 0.105 g (27%) oil.

C. [2S-[2α(E,E,E),3β]]-Tetrahydro-2-(1-methyl-6-[3-(trifluoromethyl)phenyl]-1,3,5-hexatrienyl]-2H-pyran-3-ol To a solution of the title B compound (0.10 g, 0.22 mmol) in dry tetrahydrofuran (20 mL) was added tetrabutylammonium fluoride (1.1M in tetrahydrofuran; 1.0 mL, 1.1 mmol), and the mixture was stirred for two hours at room temperature. The solvent was evaporated in vacuo and the residue dissolved in ethyl acetate. The organic solution was washed four times with water, and the combined water washings were reextracted with ethyl acetate. The combined organic layers were dried over sodium sulfate, and the solvent was evaporated in vacuo.

Yield: 0.096 g (>quant.) oil. This material was used without further purification for the subsequent reaction.

D. N-[[[2-(Trimethylsilyl)ethyl]oxy]carbonyl]glycine, [2S-[2α(E,E,E), 3β]]-tetrahydro-2-[1-methyl-6-[3-(trifluoromethyl)phenyl]-1,3,5-hexatrienyl]-2H-pyran-3-yl ester To a solution of crude title C compound (0.094 g, 0.28 mmol) in dry dichloromethane (20 mL) was added N-(trimethylsilylethoxy)carbonylglycine (0.18 g, 0.84 mmol), ethyl-3-(3-dimethylamino)propylcarbodiimide hydrochloride (0.16 g, 0.84 mmol), dimethylaminopropylamine (0.043 g, 0.35 mmol), and a trace of 2,6-ditert-butyl-4-methylphenol. The mixture was stirred for one hour at room temperature and washed three times with water. The water was reextracted with dichloromethane, and the combined organic layers were dried over sodium sulfate and evaporated in vacuo. The residue was purified by column chromatography on silica gel using ethyl acetate containing 33% pentane as eluent.

Yield: 0.043 g (10%) oil.

E. Glycine, 2S-[2α(E,E,E),3β]-tetrahydro-2-(1-methyl-6-[3-(trifluoromethyl)phenyl]-1,3,5-hexatrienyl]-2H-pyran-3-yl ester To a solution of the title D compound (0.070 g, 0.13 mmol) in dry tetrahydrofuran (5 mL) was added tetrabutylammonium fluoride (0.3 mL, 1.1M solution in tetrahydrofuran; 0.33 mmol) and the mixture stirred for 90 minutes at 40° C. The solvent was evaporated in vacuo and the residue dissolved in ethyl acetate. The organic solution was washed three times with water, and the water was reextracted with ethyl acetate. The combined organic layers were washed with brine, dried over sodium sulfate, and evaporated in vacuo. The residue was purified by column chromatography on silica gel using ethyl acetate as eluent.

Yield: 0.043 g (24%) oil.

What is claimed is:

1. A compound of the formula

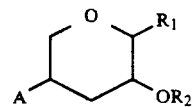

or a pharmaceutically acceptable salt thereof:
where A is hydrogen or methyl;
$R_1$ is alkyl, alkenyl, arylalkyl, arylalkenyl, carboxy,

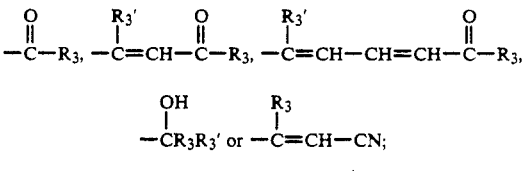

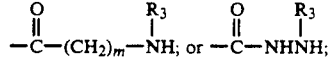

$R_2$ is

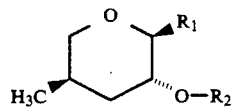

$R_3$ and $R_3'$ are independently hydrogen or alkyl; and m is an integer of 1 to 4.

2. A compound as recited in claim 1 having the structure IA

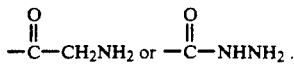

where $R_1$ is alkyl, alkenyl or arylalkenyl and $R_2$ is $$-\overset{O}{\underset{\|}{C}}-CH_2NH_2 \text{ or } -\overset{O}{\underset{\|}{C}}-NHNH_2.$$

3. A compound as recited in claim 1 having the structure IB

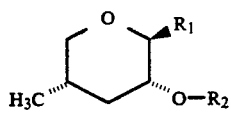

where R₁ is alkyl, alkenyl or arylalkenyl and R₂ is

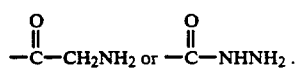

4. A compound as recited in claim 1 having the structure IC

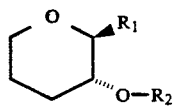

where R₁ is alkyl, alkenyl or arylalkenyl and R₂ is

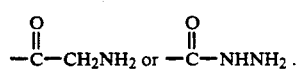

5. A compound as recited in claim 1 having the structure IA

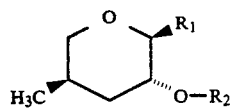

where R₁ is selected from

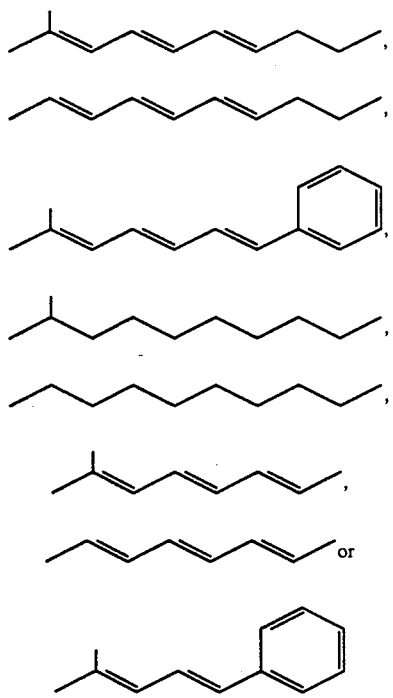

and R₂ is

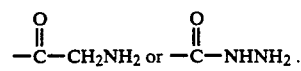

6. A compound as recited in claim 1 having the structure IB

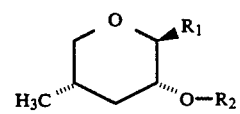

where R₁ is selected from

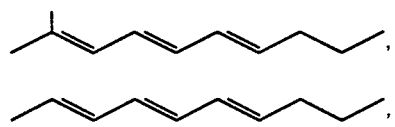

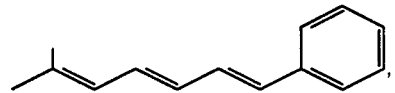

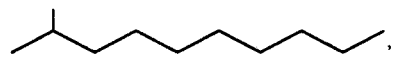

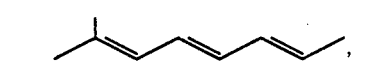

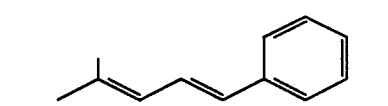

and R₂ is

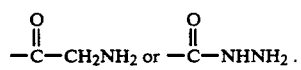

7. A compound as recited in claim 1 having the structure IC

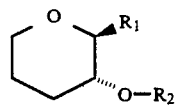

where R₁ is selected from

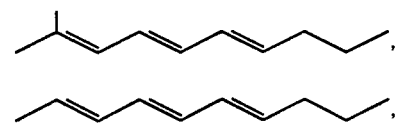

-continued

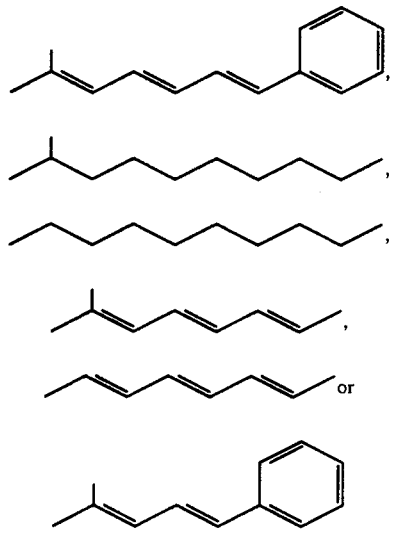

and R₂ is

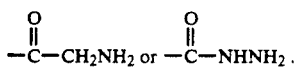

8. A compound as recited in claim 1, Glycine, [2S-[2α(E,E,E)3β,5α]]Tetrahydro-5-methyl-2-(1-methyl-1,3,5-nonatrienyl)-2H-pyran-3-yl-ester, or a pharmaceutically acceptable salt thereof.

9. A compound as recited in claim 1, Glycine, [2S-[2α(E,E,E),3β,5β]]Tetrahydro-5-methyl-2-(1-methyl-1,3,5-nonatrienyl)-2H-pyran-3-yl ester, or a pharmaceutically acceptable salt thereof.

10. A compound as recited in claim 1, Glycine, [2S-[2α(E,Z,E),3β,5α]]Tetrahydro-5-methyl-2-(1-methyl-1,3,5-nonatrienyl)-2H-pyran-3-yl ester, or a pharmaceutically acceptable salt thereof.

11. A compound as recited in claim 1, Glycine, [2S-2α(E,Z,E),3β,5β]]Tetrahydro-5-methyl-2-(1-methyl-1,3,5-nonatrienyl)-2H-pyran-3-yl ester, or a pharmaceutically acceptable salt thereof.

12. A compound as recited in claim 1, Glycine, [2S-[2α(E,E,E),3β,5α]]-Tetrahydro-5-methyl-2-(1,3,5-nonatrienyl)-2H-pyran-3-yl ester, or a pharmaceutically acceptable salt thereof.

13. A compound as recited in claim 1, Glycine, [2S-[2α(E,E,E),3β,5β]]-Tetrahydro-5-methyl-2-(1,3,5-nonatrienyl)-2H-pyran-3-yl ester, or a pharmaceutically acceptable salt thereof.

14. A compound as recited in claim 1, Glycine, [2S-(2α,3β,5β)]-tetrahydro-5-methyl-2-nonyl-2H-pyran-3-yl ester, or a pharmaceutically acceptable salt thereof.

15. A compound as recited in claim 1, Glycine, [2S-(2α,3β,5α)]-tetrahydro-5-methyl-2-nonyl-2H-pyran-3-yl ester, or a pharmaceutically acceptable salt thereof.

16. A compound as recited in claim 1, Glycine, [2S-[2α(1E,3Z,5E),3β]]-Tetrahydro-2-(1-methyl-1,3,5-nonatrienyl)-2H-pyran-3-yl ester, or a pharmaceutically acceptable salt thereof.

17. A compound as recited in claim 1, Glycine, [2S-[2α(E,E,E),3β]]-Tetrahydro-2-(1-methyl-1,3,5-nonatrienyl)-2H-pyran-3-yl ester, or a pharmaceutically acceptable salt thereof.

18. A compound as recited in claim 1, Glycine, (2S-trans)-tetrahydro-2-(1-methylnonyl)-2H-pyran-3-yl ester, or a pharmaceutically acceptable salt thereof.

19. A compound as recited in claim 1, Glycine, [2S-[2α(E,E,E),3β]]-tetrahydro-2-[1-methyl-6-[2-naphthalenyl]-1,3,5-hexatrienyl]-2H-pyran-3-yl ester, or a pharmaceutically acceptable salt thereof.

20. A compound as recited in claim 1, Glycine, [2S-[2α(E,E,E),3β]]-tetrahydro-2-(1-methyl-6-[3-(trifluoromethyl)phenyl]-1,3,5-hexatrienyl]-2H-pyran-3-yl ester, or a pharmaceutically acceptable salt thereof.

21. A pharmaceutical composition comprising a compound of claim 1 and a pharmaceutically acceptable carrier.

22. A method of treating a fungal infection in a plant specie comprising administering to a specie in need thereof a therapeutically effective amount of a composition of claim 21.

23. A method of treating a fungal infection in a mammalian specie comprising administering to a specie in need thereof a therapeutically effective amount of a composition of claim 21.

* * * * *